United States Patent
Fish et al.

(10) Patent No.: US 9,095,349 B2
(45) Date of Patent: Aug. 4, 2015

(54) SYSTEMS AND METHODS FOR DETERMINING THE LIKELIHOOD OF ENDOCARDIAL BAROTRAUMA IN TISSUE DURING ABLATION

(75) Inventors: Jeffrey M. Fish, Maple Grove, MN (US); Israel A. Byrd, Richfield, MN (US); Lynn Gilmour, Savage, MN (US); Jeremy D. Dando, Plymouth, MN (US); Christopher J. Geurkink, Minnetonka, MN (US); Rohan Lathia, Westford, MA (US); Harry A. Puryear, Shoreview, MN (US); Valtino X. Afonso, Oakdale, MN (US); Saurav Paul, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1211 days.

(21) Appl. No.: 12/964,956

(22) Filed: Dec. 10, 2010

(65) Prior Publication Data
US 2011/0144657 A1    Jun. 16, 2011

Related U.S. Application Data

(60) Provisional application No. 61/285,756, filed on Dec. 11, 2009.

(51) Int. Cl.
*A61B 5/053*  (2006.01)
*A61B 18/14*  (2006.01)
(Continued)

(52) U.S. Cl.
CPC ........... *A61B 18/1492* (2013.01); *A61B 5/0538* (2013.01); *A61B 5/036* (2013.01);
(Continued)

(58) Field of Classification Search
CPC ........... A61B 2017/00026; A61B 2018/00351; A61B 2018/00702; A61B 2018/00875; A61B 5/0538
USPC ..................................................... 606/34–38
See application file for complete search history.

(56) References Cited

U.S. PATENT DOCUMENTS 5,295,484 A   3/1994  Marcus et al.
5,718,701 A   2/1998  Shai et al.
(Continued)

FOREIGN PATENT DOCUMENTS

EP   1174080         1/2002
WO   2007/067628     6/2007
WO   WO-2009/065140  5/2009

OTHER PUBLICATIONS

"International Search Report and Written Opinion of the International Searching Authority", PCT/US2010/059884 Feb. 14, 2011.
(Continued)

*Primary Examiner* — Jaymi Della
(74) *Attorney, Agent, or Firm* — Dykema Gossett PLLC

(57) ABSTRACT

A method and system for determining a likelihood of barotrauma occurring in tissue during formation of a lesion therein is provided. The system includes an electronic control unit (ECU). The ECU is configured to acquire at least one value of at least one component of a complex impedance between an electrode and the tissue. The ECU is configured to calculate an index responsive to the at least one value of the at least one complex impedance component. The index is indicative of a likelihood of barotrauma occurring in the tissue. The method comprises acquiring at least one value of at least one component of a complex impedance between an electrode and the tissue. The method comprises calculating an index responsive to the at least one value of the at least one complex impedance component. The calculated index is indicative of a likelihood of barotrauma occurring in the tissue.

23 Claims, 16 Drawing Sheets

(51) Int. Cl.
    *A61B 17/00* (2006.01)
    *A61B 18/00* (2006.01)
    *A61B 19/00* (2006.01)
    *A61B 5/03* (2006.01)

(52) U.S. Cl.
    CPC ........... *A61B2017/00026* (2013.01); *A61B 2017/00119* (2013.01); *A61B 2018/00351* (2013.01); *A61B 2018/00702* (2013.01); *A61B 2018/00875* (2013.01); *A61B 2019/2211* (2013.01); *A61B 2019/505* (2013.01); *A61B 2019/5229* (2013.01); *A61B 2019/5251* (2013.01); *A61B 2019/5253* (2013.01)

(56) References Cited

U.S. PATENT DOCUMENTS

| | | |
|---|---|---|
| 6,233,476 B1 | 5/2001 | Strommer et al. |
| 6,498,944 B1 | 12/2002 | Ben-Haim et al. |
| 6,690,963 B2 | 2/2004 | Ben-Haim et al. |
| 6,788,967 B2 | 9/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |
| 7,536,218 B2 | 5/2009 | Govari et al. |
| 2001/0039419 A1* | 11/2001 | Francischelli et al. .......... 606/42 |
| 2002/0068931 A1 | 6/2002 | Wong et al. |
| 2007/0016006 A1 | 1/2007 | Shachar |
| 2007/0173805 A1* | 7/2007 | Weinberg et al. .............. 606/34 |
| 2009/0163904 A1 | 6/2009 | Miller et al. |
| 2009/0247993 A1 | 10/2009 | Kirschenman et al. |
| 2009/0275827 A1 | 11/2009 | Aiken et al. |
| 2010/0069921 A1 | 3/2010 | Miller et al. |
| 2010/0168550 A1 | 7/2010 | Byrd et al. |
| 2010/0168572 A1* | 7/2010 | Sliwa et al. .................. 600/439 |

OTHER PUBLICATIONS

Arruda, Mauricio et al., "Impedance Phase Angle Optimizes Electrode-Tissue Contact and is Superior to Contact Force to Predict RF Lesion Formation and Tissue Popping: Improving Safety and Efficacy of Ablation Using Open Irrigation Catheters," OASIS—Online Abstract Submission and Invitation System, www.abstractsonline.com/viewer/viewAbstractPrintFirnedly.asp?CKey={52CAC5CD-1B17-4A3A . . . Mar. 25, 2008.

Seiler, Jens et al., "Steam pops during irrigated radiofrequency ablation: Feasibility of impedance monitoring for prevention," Heart Rhythm Journal, vol. 5, Issue 10, pp. 1411-1416, Oct. 2008 (published online Jul. 11, 2008).

Supplementary Eurpopean Search Report in EP Application No. 10836750.9 (Jul. 2, 2014).

* cited by examiner

| TIME (t) | RESISTANCE (R) | REACTANCE (X) | POWER (P) |
|---|---|---|---|
| $t_0$ | $R_0$ | -- | -- |
| $t_1$ | $R_1$ | $X_1$ | $P_1$ |
| $t_2$ | $R_2$ | $X_2$ | $P_2$ |
| $t_3$ | $R_3$ | $X_3$ | $P_3$ |
| ⋮ | ⋮ | ⋮ | ⋮ |
| $t_n$ | $R_n$ | $X_n$ | $P_n$ |

FIG.8

SYSTEMS AND METHODS FOR DETERMINING THE LIKELIHOOD OF ENDOCARDIAL BAROTRAUMA IN TISSUE DURING ABLATION

CROSS REFERENCE TO RELATED APPLICATIONS

This application claims the benefit of U.S. Provisional Patent Application No. 61/285,756 entitled "System and Method for Determining the Likelihood of Endocardial Barotrauma in Tissue During Ablation," filed on Dec. 11, 2009, now pending, and hereby incorporated by reference in its entirety.

BACKGROUND OF THE INVENTION a. Field of the Invention

This disclosure relates to a system, method of manufacturing, and method for determining the likelihood of barotrauma occurring in tissue during an ablation procedure performed on the tissue. More particularly, the instant disclosure relates to a system and method for determining the likelihood of endocardial barotrauma occurring in cardiac tissue during the formation of a lesion therein as a result of an ablation procedure being performed thereon b. Background Art During ablation procedures, such as, for example, cardiac ablation procedures, adverse events may occur resulting in damage to the tissue being ablated (e.g., charring of the tissue and localized coagulation) that, in turn, may result in even worse consequences such as stroke or death. In RF ablation, one such adverse event, though rare, is the occurrence of endocardial barotrauma, or "steam pops." Endocardial barotrauma may occur, for example, when water in the blood and/or tissue boils as a result of the RF energy applied to the tissue. Accordingly, it is desirable to be able to predict or determine when events, such as endocardial barotrauma, are going to occur before they occur in order to take preventive measures. Unfortunately, in conventional or current systems the risk or likelihood of endocardial barotrauma occurring is not consistently evaluated or determined.

One conventional means for assessing the risk or likelihood of endocardial barotrauma occurrence is to monitor tissue temperature during an ablation procedure. Endocardial barotrauma occurs due to heating of the cardiac tissue above 100° C. during application of RF energy or power, however, no accurate means exists to measure tissue temperature. Some conventional systems may contain a thermistor, thermocouple, or some other temperature sensor in the tip of the ablation catheter, however, factors, such as blood flow or saline irrigation, for example, significantly affect the tip temperature, thereby making these temperature values difficult to interpret.

Other convention means by which endocardial barotrauma occurrence is prevented, or at least the risk of occurrence is managed, include monitoring the impedance drop during the RF delivery, and/or limiting the RF power being delivered to the tissue. These means or methodologies have proved to be less than optimal in the prediction or determination of the likelihood of endocardial barotrauma occurring in the tissue.

Accordingly, the inventors herein have recognized a need for a system and method for determining the likelihood of endocardial barotrauma occurring in tissue during the formation of a lesion therein as a result of an ablation procedure being performed thereon that will minimize and/or eliminate one or more of the deficiencies in conventional ablation systems.

BRIEF SUMMARY OF THE INVENTION

The present invention is directed to a method and system for determining a likelihood of barotrauma occurring in a tissue during the formation of a lesion therein as a result of an ablation procedure being performed thereon. The system according to the present teachings includes an electronic control unit. The electronic control unit is configured to acquire at least one value of at least one component of a complex impedance between an electrode and the tissue. In an exemplary embodiment, the electronic control unit is further configured to acquire a value for the power applied to the tissue during the formation of the lesion in the tissue. The electronic control unit is still further configured to calculate an index responsive to the value(s) of the at least one complex impedance component, and, in an exemplary embodiment, the value of the power. The index is indicative of a likelihood of barotrauma occurring in the tissue.

In accordance with another aspect of the invention, an article of manufacture is provided. The article of manufacture, in accordance with the present teachings, includes a computer-readable storage medium having a computer program encoded thereon for determining a likelihood of barotrauma occurring in a tissue during the formation of a lesion in the tissue as a result of an ablation procedure being performed on the tissue. The computer program includes code for calculating an index responsive to one or more values of at least one component of a complex impedance between an electrode and the tissue, and, in an exemplary embodiment, a value of the power applied to the tissue during the formation of the lesion therein.

In accordance with still another aspect of the invention, a method for determining a likelihood of barotrauma occurring in a tissue during the formation of a lesion therein as a result of an ablation procedure being performed thereon is provided. In accordance with the present teachings, the method includes a step of acquiring at least one value for at least one component of a complex impedance between an electrode and the tissue. In an exemplary embodiment, the method further includes a step of acquiring a value of the power applied to the tissue during the formation of the lesion therein. The method still further includes a step of calculating an index responsive to the value(s) of the at least one complex impedance component, and, in an exemplary embodiment, the value of the power, wherein the index is indicative of a likelihood of barotrauma occurring in the tissue.

In accordance with yet still another aspect of the invention, an automated guidance system is provided. The system, in accordance with present teachings, includes a catheter manipulator assembly and a catheter associated therewith that is configured to deliver RF power to a tissue in a body through an electrode. The system further includes a controller configured to control at least one of the movement of the catheter and the delivery of RF power to the tissue by the electrode in response to an index calculated from value(s) of at least one component of a complex impedance between the electrode and the tissue, and, in an exemplary embodiment, a value of RF power applied to the tissue during the formation of a lesion in the tissue.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 8 is a table showing an exemplary embodiment of how data acquired by the system of FIG. 1 is organized and/or stored.

DETAILED DESCRIPTION OF EMBODIMENTS OF THE INVENTION

Figure 1:
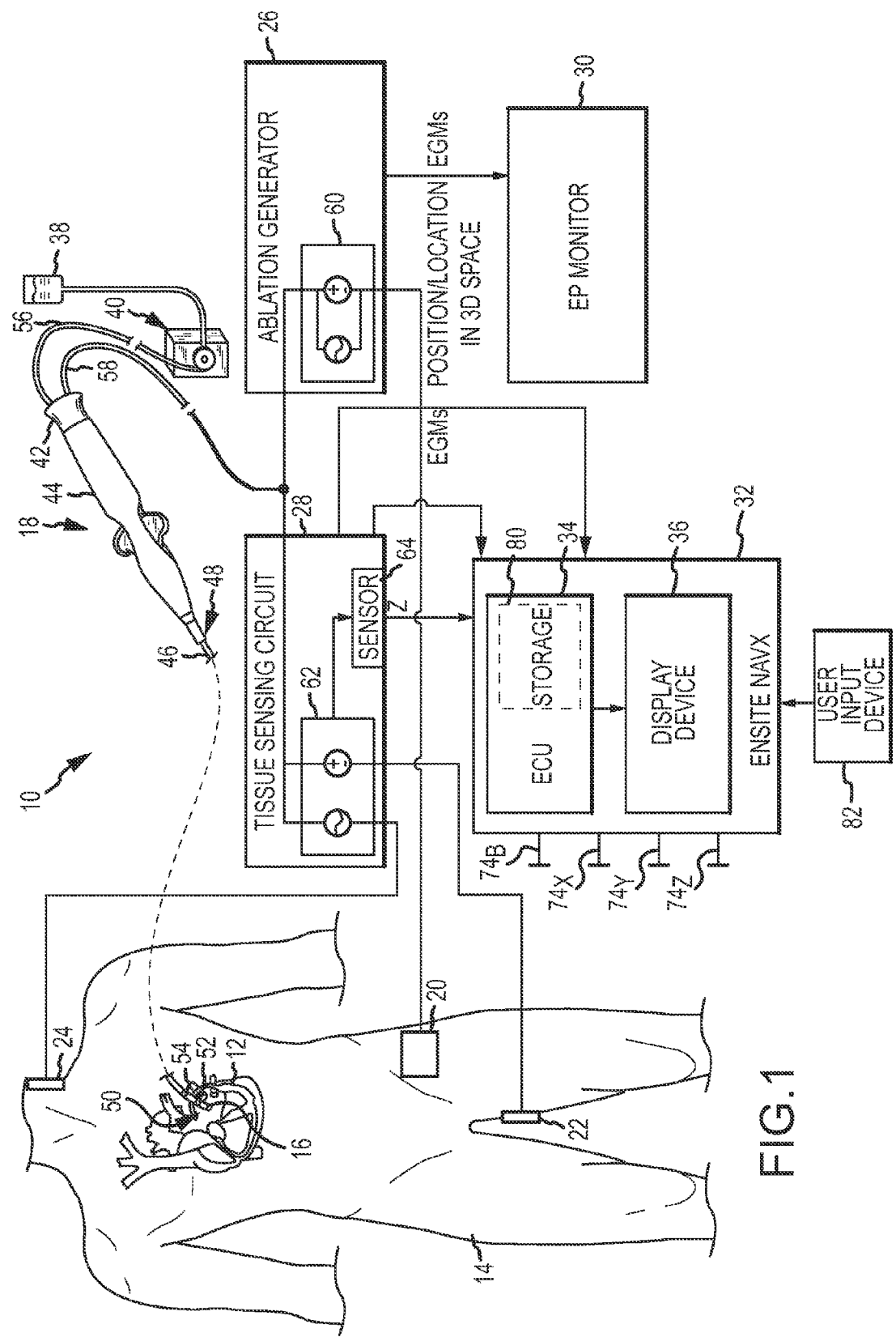
FIG. 1 is diagrammatic view of a system in accordance with the present teachings.

Referring now to the drawings wherein like reference numerals are used to identify identical components in the various views, FIG. 1 illustrates one exemplary embodiment of a system 10 configured, at least in part, for determining a likelihood of barotrauma (also referred to in the art as "steam pop" or "steam pops") occurring in a tissue 12 of a body 14 during an ablation procedure. More particularly, the system 10 is configured to determine the likelihood of barotrauma occurring in the tissue 12 during the formation of a lesion therein as a result of an ablation procedure being performed thereon. In an exemplary embodiment wherein the tissue 12 is cardiac tissue, the system 10 is configured to determine the likelihood of endocardial barotrauma occurring in the tissue 12 being ablated by radio frequency (RF) energy or power delivered from an electrode 16 disposed on a catheter 18. For the sake of clarity and brevity alone, the description set forth below will be with respect to cardiac tissue only. It should be understood, however, that the present disclosure may find application in connection with determining a likelihood of barotrauma occurring in other types of tissue during ablation procedures. Accordingly, the application of the present disclosure is not meant to be limited to that of cardiac tissue.

In addition to the electrode 16 and the catheter 18, the system 10 may include patch electrodes 20, 22, 24, an ablation generator 26, a tissue sensing circuit 28, an electrophysiology (EP) monitor 30, and a system 32 for visualization, mapping, and navigation of internal body structures, which may include an electronic control unit 34 in accordance with the present disclosure, and a display device 36, among other components.

The catheter 18 is provided for examination, diagnosis and treatment of internal body tissues such as the tissue 12. In accordance with one embodiment, the catheter 18 comprises an ablation catheter and, more particularly, an irrigated radio-frequency (RF) ablation catheter. In an exemplary embodiment, the catheter 18 is connected to a fluid source 38 having a biocompatible fluid, such as saline through a pump 40 (which may comprise, for example, a fixed rate roller pump or variable volume syringe pump with a gravity feed supply from the fluid source 38 as shown), for irrigation. It should be noted, however, that the present disclosure is not meant to be limited to irrigated catheters, but rather it may find applicability with any number of electrode and ablation device combinations. In an exemplary embodiment, the catheter 18 is also electrically connected to the ablation generator 26 for delivery of RF energy or power. The catheter 18 may include a cable connector or interface 42, a handle 44, a shaft 46 having a proximal end 48 and a distal 50 end (as used herein, "proximal" refers to a direction toward the end of the catheter near the clinician, and "distal" refers to a direction away from the clinician and (generally) inside the body of a patient) and one or more electrodes 16, 52, 54. The catheter 18 may also include other conventional components not illustrated herein, such as, for example, a temperature sensor, additional electrodes, and corresponding conductors or leads, or additional ablation elements (e.g., a high intensity focused ultrasound ablation element).

The connector 42 provides mechanical, fluid and electrical connection(s) for cables 56, 58 extending from the pump 40 and the ablation generator 26. The connector 42 is conventional in the art and is disposed at the proximal end 48 of the catheter 18.

The handle 44 provides a location for the clinician to hold the catheter 18 and may further provide a means for steering or the guiding of the shaft 46 within the body 14. For example, the handle 44 may include means to change the length of a guidewire extending through the catheter 18 to the distal end 50 of the shaft 46 to steer the shaft 46. The handle 44 is also conventional in the art and it will be understood that the construction of the handle 44 may vary. In an alternate exemplary embodiment to be described in greater detail below, the catheter 18 may be robotically or magnetically driven or controlled. Accordingly, rather than a clinician manipulating a handle to steer or guide the catheter 18, and the shaft 46 thereof, in particular, a robot or a magnetic-based system is used to manipulate the catheter 18.

The shaft 46 is an elongated, tubular, flexible member configured for movement within the body 14. The shaft 46 supports the electrodes 16, 52, 54, associated conductors, and possibly additional electronics used, for example, for signal processing or conditioning. The shaft 46 may also permit transport, delivery and/or removal of fluids (including irrigation fluids, cryogenic ablation fluids, and bodily fluids), medicines, and/or surgical tools or instruments. The shaft 46 may be made from conventional materials such as polyurethane and defines one or more lumens configured to house and/or transport electrical conductors, fluids or surgical tools. The shaft 46 may be introduced into a blood vessel or other structure within the body 14 through a conventional introducer. The shaft 46 may then be steered or guided through the body 14 to a desired location such as the tissue 12 with guidewires or other means known in the art.

The electrodes 16, 52, 54 are provided for a variety of diagnostic and therapeutic purposes including, for example, electrophysiological studies, catheter identification and location, pacing, cardiac mapping, and ablation. In the illustrated embodiment, the catheter 18 includes an ablation tip electrode 16 at the distal end 50 of the shaft 46, and a pair of ring electrodes 52, 54. It should be understood, however, that the number, shape, orientation, and purpose of the electrodes 16, 52, 54 may vary.

The patch electrodes 20, 22, 24 provide RF or navigational signal injection paths and/or are used to sense electrical potentials. The electrodes 20, 22, 24 may also have additional purposes such as the generation of an electromechanical map. The electrodes 20, 22, 24 are made from flexible, electrically conductive material and are configured for affixation to the body 14 such that the electrodes 20, 22, 24 are in electrical contact with the patient's skin. The electrode 20 may function as an RF indifferent/dispersive return for the RF ablation signal. The electrodes 22, 24 may function as returns for the RF ablation signal source and/or an excitation signal generated by the tissue sensing circuit 28 as described in greater detail hereinbelow. In accordance with one aspect of the present disclosure discussed hereinbelow, the electrodes 22, 24 are preferably spaced relatively far apart. In the illustrated embodiment, the electrodes 22, 24, are located on the medial aspect of the left leg and the dorsal aspect of the neck. The electrodes 22, 24, may alternatively be located on the front and back of the torso or in other conventional orientations.

The ablation generator 26 generates, delivers, and controls RF energy output by the ablation catheter 18, and the electrode 16, in particular. The generator 26 is conventional in the art and may comprise the commercially available unit sold under the model number IBI-1500T-11 RF Cardiac Ablation Generator, available from Irvine Biomedical, Inc. The generator 26 includes an RF ablation signal source 60 configured to generate an ablation signal that is output across a pair of source connectors: a positive polarity connector SOURCE (+) which may connect to the tip electrode 16; and a negative polarity connector SOURCE(−) which may be electrically connected by conductors or lead wires to one of the patch electrodes 20, 22, 24 (see FIG. 2). It should be understood that the term connectors as used herein does not imply a particular type of physical interface mechanism, but is rather broadly contemplated to represent one or more electrical nodes. The source 60 is configured to generate a signal at a predetermined frequency in accordance with one or more user specified parameters (e.g., power, time, etc.) and under the control of various feedback sensing and control circuitry as is know in the art. The source 60 may generate a signal, for example, with a frequency of about 450 kHz or greater. The generator 26 may also monitor various parameters associated with the ablation procedure including impedance, the temperature at the tip of the catheter, ablation energy, and the position of the catheter and provide feedback to the clinician regarding these parameters. The impedance measurement output by a typical currently available reflects the magnitude of impedance not only at the tissue 12, but the entire impedance between the tip electrode 16 and the corresponding patch electrode 20 on the body surface. In an exemplary embodiment, the ablation generator 26 may generate a higher frequency current for the purposes of RF ablation, and a second lower frequency current for the purpose of measuring impedance.

The tissue sensing circuit 28 provides a means, such as a tissue sensing signal source 62, for generating an excitation signal used in impedance measurements and means, such as a complex impedance sensor 64, for resolving the detected impedance into its component parts. In another exemplary embodiment, the complex impedance may be measured using components other than the tissue sensing circuit 28, such as, for example, the ablation generator 26. However, in an embodiment wherein the tissue sensing circuit is used, the signal source 62 is configured to generate an excitation signal across source connectors SOURCE (+) and SOURCE (−) (See FIG. 2). The source 62 may output a signal having a frequency within a range from about 1 kHz to over 500 kHz, more preferably within a range of about 2 kHz to 200 kHz, and even more preferably about 20 kHz. In one embodiment, the excitation signal is a constant current signal, preferably in the range of between 20-200 µA, and more preferably about 100 µA. As discussed below, the constant current AC excitation signal generated by the source 62 is configured to develop a corresponding AC response voltage signal that is dependent on the complex impedance of the tissue 12 and is sensed by the complex impedance sensor 64. The sensor 64 resolves the complex impedance into its component parts (i.e., the resistance (R) and reactance (X) or the impedance magnitude (|Z|) and phase angle (∠Z or ϕ)). Sensor 64 may include conventional filters (e.g., bandpass filters) to block frequencies that are not of interest, but permit appropriate frequencies, such as the excitation frequency, to pass, as well as conventional signal processing software used to obtain the component parts of the measured complex impedance.

It should be understood that variations are contemplated by the present disclosure. For example, the excitation signal may be an AC voltage signal where the response signal comprises an AC current signal. Nonetheless, a constant current excitation signal is preferred as being more practical. It should be appreciated that the excitation signal frequency is preferably outside of the frequency range of the RF ablation signal, which allows the complex impedance sensor 64 to more readily distinguish the two signals, and facilitates filtering and subsequent processing of the AC response voltage signal. The excitation signal frequency is also preferably outside the frequency range of conventionally expected electrogram (EGM) signals in the frequency range of 0.05 Hz-1 kHz. Thus, in summary, the excitation signal preferably has a frequency that is preferably above the typical EGM signal frequencies and below the typical RF ablation signal frequencies. Additionally, in certain embodiments multiple excitation signals of different frequencies may be used to determine multiple complex impedances. For example, in one exemplary embodiment, a 20 kHz signal and a 200 kHz signal may be generated and a complex impedance corresponding to each may be determined and used as will be described below. Accordingly, the present disclosure is not limited to an embodiment wherein a single excitation signal is employed, but rather includes embodiments wherein multiple excitation signals are used. For the sake of clarity and brevity, however, the following description will be limited to the embodiment wherein a single excitation signal is use.

The circuit 28 is also connected, for a purpose described hereinbelow, across a pair of sense connectors: a positive polarity connector SENSE (+) which may connect to the tip electrode 16; and a negative polarity connector SENSE (−) which may be electrically connected to one of the patch electrodes 20, 22, 24 (see FIG. 2; note, however, that the connector SENSE (−) should be connected to a different electrode of the electrodes 20, 22, 24 relative to the connector SOURCE (−) as discussed below). It should again be understood that the term connectors as used herein does not imply a particular type of physical interface mechanism, but is rather broadly contemplated to represent one or more electrical nodes.

Figure 2:
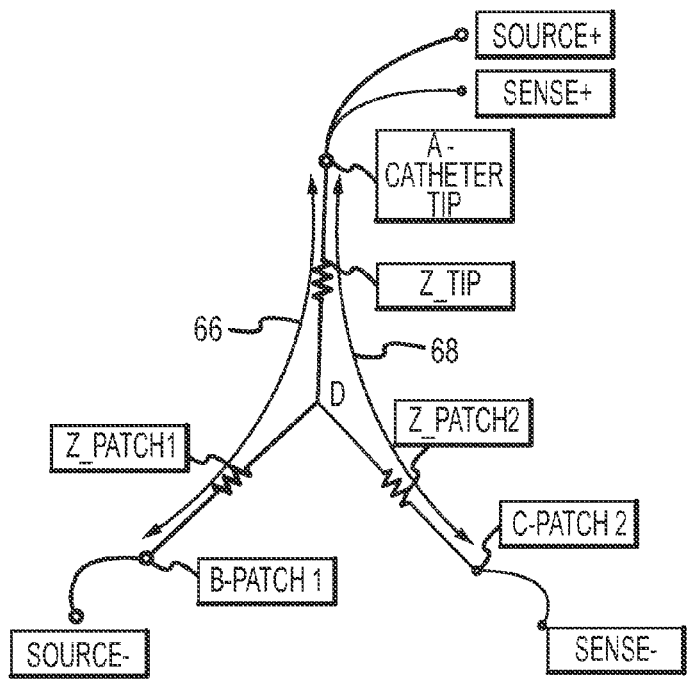
FIG. 2 is a simplified schematic diagram illustrating how impedance is determined in accordance with the present teachings.

Referring now to FIG. 2, connectors SOURCE (+), SOURCE (−), SENSE (+) and SENSE (−) form a three-terminal arrangement permitting measurement of the complex impedance at the interface of the tip electrode 16 and the tissue 12. Complex impedance can be expressed in rectangular coordinates as set forth in equation (1):

$$Z = R + jX \quad (1)$$

where R is the resistance component (expressed in ohms); and X is a reactance component (also expressed in ohms). Complex impedance can also be expressed polar coordinates as set forth in equation (2):

$$Z = r \cdot e^{j\theta} = |Z| \cdot e^{j \angle Z} \quad (2)$$

where |Z| is the magnitude of the complex impedance (expressed in ohms) and $\angle Z = \theta$ is the phase angle expressed in radians. Alternatively, the phase angle may be expressed in terms of degrees where $$\phi = \left(\frac{180}{\pi}\right)\theta.$$

Throughout the remainder of this specification, phase angle will be preferably referenced in terms of degrees. The three terminals comprise: (1) a first terminal designated "A-Catheter Tip" which is the tip electrode 16; (2) a second terminal designated "B-Patch 1" such as the source return patch electrode 24; and (3) a third terminal designated "C-Patch 2" such as the sense return patch electrode 22. In addition to the ablation (power) signal generated by the source 60 of the ablation generator 26, the excitation signal generated by the source 62 in the tissue sensing circuit 28 is also be applied across the source connectors (SOURCE (+), SOURCE(−)) for the purpose of inducing a response signal with respect to the load that can be measured and which depends on the complex impedance.

As described above, in one embodiment, a 20 kHz, 100 μA AC constant current signal is sourced along a path 66, as illustrated, from one connector (SOURCE (+), starting at node A) through the common node (node D) to a return patch electrode (SOURCE (−), node B). The complex impedance sensor 64 is coupled to the sense connectors (SENSE (+), SENSE (−)), and is configured to determine the impedance across a path 68. For the constant current excitation signal of a linear circuit, the impedance will be proportional to the observed voltage developed across SENSE (+)/SENSE(−), in accordance with Ohm's Law: Z=V/I. Because voltage sensing is nearly ideal, the current flows through the path 66 only, so the current through the path 68 (node D to node C) due to the excitation signal is effectively zero. Accordingly, when measuring the voltage along the path 68, the only voltage observed will be where the two paths intersect (i.e., from node A to node D). Depending on the degree of separation of the two patch electrodes (i.e., those forming nodes B and C), an increasing focus will be placed on the tissue volume nearest the tip electrode 16. If the patch electrodes are physically close to each other, the circuit pathways between the catheter tip electrode 16 and the patch electrodes will overlap significantly and impedance measured at the common node (i.e., node D) will reflect impedances not only at the interface of the catheter electrode 16 and the tissue 12, but also other impedances between the tissue 12 and the surface of body 14. As the patch electrodes are moved further apart, the amount of overlap in the circuit paths decreases and impedance measured at the common node is only at or near the tip electrode 16 of the catheter 18.

Figure 3:
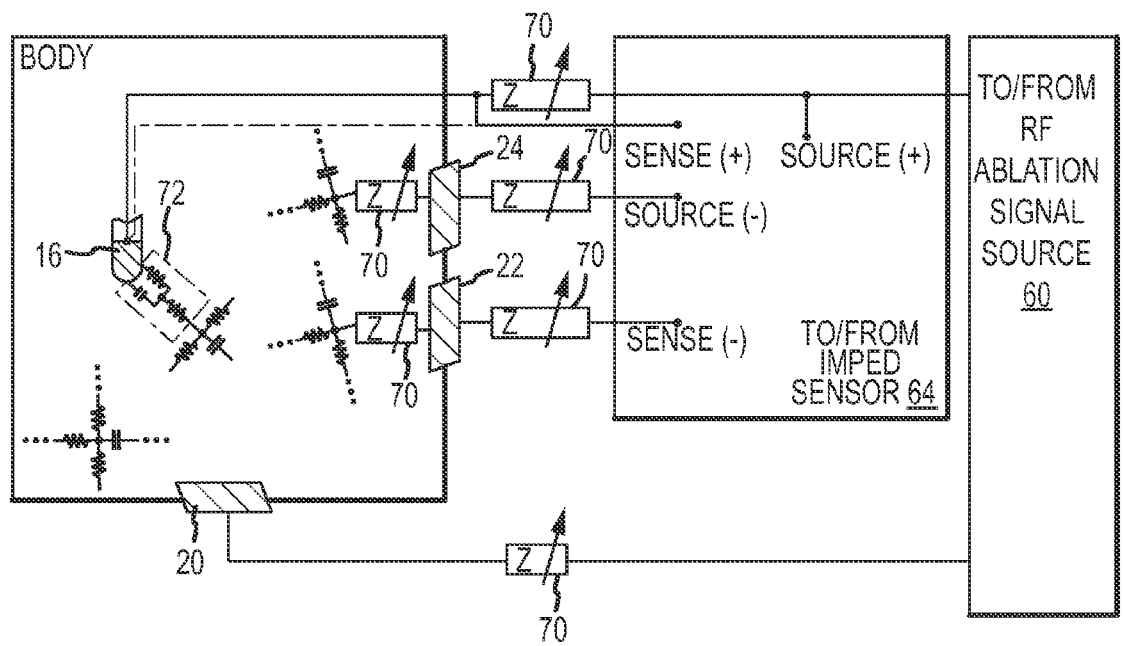
FIG. 3 is a diagrammatic and block diagram illustrating the approach in FIG. 2 in greater detail.

Referring now to FIG. 3, the concept illustrated in FIG. 2 is extended. FIG. 3 is a simplified schematic and block diagram of a three-terminal measurement arrangement. For clarity, it should be pointed out that the SOURCE (+) and SENSE (+) lines may be joined in the catheter connector 42 or the handle 44 (as in solid line) or may remain separate all the way to the tip electrode 16 (the SENSE (+) line being shown in phantom line from the handle 44 to the tip electrode 16). FIG. 3 shows, in particular, several sources of complex impedance variations, shown generally as blocks 70, that are considered "noise" because such variations do not reflect the physiologic changes in the tissue 12 whose complex impedance is being measured. For reference, the tissue 12 whose complex impedance is being measured is that near and around the tip electrode 16 and is enclosed generally by a phantom-line box 72 (and the tissue 12 is shown schematically, in simplified form, as a resistor/capacitor combination). One object is to provide a measurement arrangement that is robust or immune to variations that are not due to changes in or around the box 72. For example, the variable complex impedance boxes 70 that are shown in series with the various cable connections (e.g., in the SOURCE (+) connection, in the SOURCE (−) and SENSE (−) connections, etc.) may involve resistive/inductive variations due to cable length changes, cable coiling and the like. The variable complex impedance boxes 70 that are near the patch electrodes 22, 24, may be more resistive/capacitive in nature, and may be due to body perspiration and the like over the course of a study. As will be seen, the various arrangements are relatively immune to the variations in the blocks 70, exhibiting a high signal-to-noise (S/N) ratio as to the complex impedance measurement for the block 72.

Although the SOURCE (−) and SENSE (−) returns are illustrated in FIG. 3 as patch electrodes 22, 24, it should be understood that other configurations are possible. In particular, the indifferent/dispersive return electrode 20 can be used as a return as well as another electrode 52, 54 on the catheter 18 as described in commonly assigned U.S. patent application Ser. No. 11/966,232 filed on Dec. 28, 2007 and titled "System and Method for Measurement of an Impedance using a Cather such as an Ablation Catheter," the entire disclosure of which is incorporated herein by reference.

The EP monitor 30 is provided to display electrophysiology data including, for example, an electrogram. The monitor 30 is conventional in the art and may comprise an LCD or CRT monitor or another conventional monitor. The monitor 30 may receive inputs from the ablation generator 26 as well as other conventional EP lab components not shown in the illustrated embodiment.

The system 32 is provided for visualization, mapping, and/or navigation of internal body structures. The system 32 may comprise an electric field-based system, such as, for example, the EnSite NavX™ system commercially available from St. Jude Medical, Inc., and as generally shown with reference to U.S. Pat. No. 7,263,397 entitled "Method and Apparatus for Catheter Navigation and Location and Mapping in the Heart," the disclosure of which is incorporated herein by reference in its entirety. In other exemplary embodiments, however, the system 32 may comprise systems other than electric field-based systems. For example, the system 32 may comprise a magnetic field-based system such as the Carto™ system commercially available from Biosense Webster, and as generally shown with reference to one or more of U.S. Pat. Nos. 6,498, 944 entitled "Intrabody Measurement;" 6,788,967 entitled "Medical Diagnosis, Treatment and Imaging Systems;" and 6,690,963 entitled "System and Method for Determining the Location and Orientation of an Invasive Medical Instrument," the disclosures of which are incorporated herein by reference in their entireties. In another exemplary embodiment, the system 32 may comprise a magnetic field-based system such as the gMPS system commercially available from MediGuide Ltd., and as generally shown with reference to one or more of U.S. Pat. Nos. 6,233,476 entitled "Medical Positioning System;" 7,197,354 entitled "System for Determining the Position and Orientation of a Catheter;" and 7,386,339 entitled "Medical Imaging and Navigation System," the disclosures of which are incorporated herein by reference in their entireties. In yet another embodiment, the system 32 may comprise a combination electric field-based and magnetic field-based system, such as, for example and without limitation, the Carto 3™ system also commercially available from Biosense Webster, and as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the system 32 may comprise or be used in conjunction with other commonly available systems, such as, for example and without limitation, fluoroscopic, computed tomography (CT), and magnetic resonance imaging (MRI)-based systems. For purposes of clarity and illustration only, the system 32 will be described hereinafter as comprising an electric field-based system, such as, for example, the EnSite NavX™ system identified above.

Figure 4:
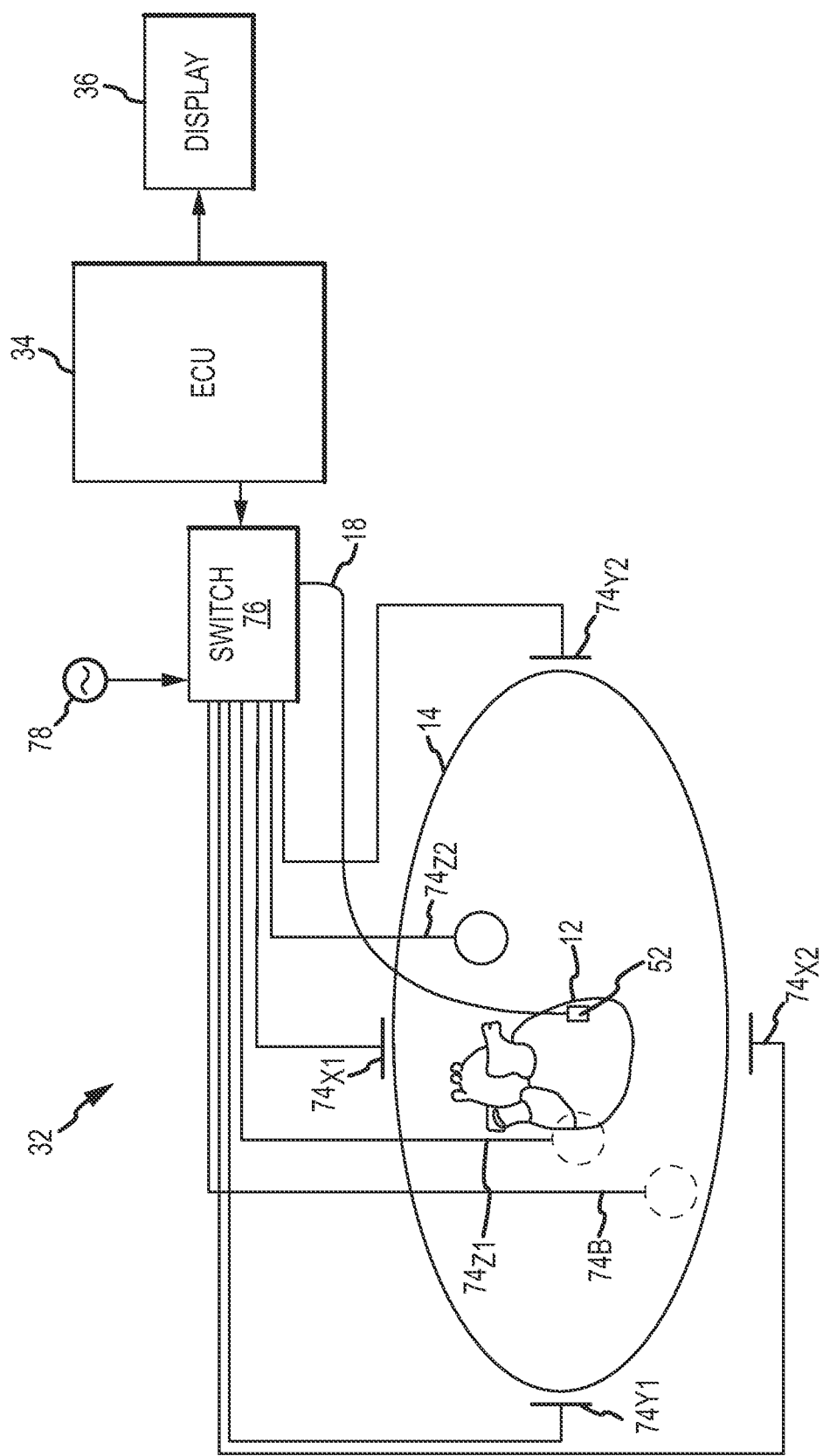
FIG. 4 is a simplified schematic diagram illustrating the visualization, navigation, and mapping system of the system illustrated in FIG. 1.

With reference to FIGS. 1 and 4, the system 32 may include a plurality of patch electrodes 74, the ECU 34, and the display device 36, among other components. However, as briefly described above, in another exemplary embodiment, the ECU 34 and/or the display device 36 may be separate and distinct components that are electrically connected to, and configured for communication with, the system 32.

With the exception of the patch electrode $74_B$ called a "belly patch," the patch electrodes 74 are provided to generate electrical signals used, for example, in determining the position and orientation of the catheter 18 and in the guidance thereof. In one embodiment, the patch electrodes 74 are placed orthogonally on the surface of the body 14 and are used to create axes-specific electric fields within the body 14. For instance, in one exemplary embodiment, patch electrodes $74_{x1}$, $74_{x2}$ may be placed along a first (x) axis. Patch electrodes $74_{Y1}$, $74_{Y2}$ may be placed along a second (y) axis, and patch electrodes $74_{Z1}$, $74_{Z2}$ may be placed along a third (z) axis. Each of the patch electrodes 74 may be coupled to a multiplex switch 76. In an exemplary embodiment, the ECU 34 is configured, through appropriate software, to provide control signals to switch 76 to thereby sequentially couple pairs of electrodes 74 to a signal generator 78. Excitation of each pair of electrodes 74 generates an electrical field within body 14 and within an area of interest such as tissue 12. Voltage levels at non-excited electrodes 74, which are referenced to the belly patch $74_B$, are filtered and converted and provided to ECU 34 for use as reference values.

As briefly discussed above, the catheter 18 includes one or more electrodes mounted therein or thereon (i.e., electrodes 16, 52, 54). In an exemplary embodiment, at least one of the electrodes comprises a positioning electrode and is configured to be electrically coupled to the ECU 34. In an exemplary embodiment, the electrode 52 comprises a positioning electrode (positioning electrode 52). With the positioning electrode 52 electrically coupled to the ECU 34, the positioning electrode 52 is placed within electrical fields created in the body 14 (e.g., within the heart) by exciting the patch electrodes 74. The positioning electrode 52 experiences voltages that are dependent on the location between the patch electrodes 74 and the position of the positioning electrode 52 relative to tissue 12. Voltage measurement comparisons made between the electrode 52 and the patch electrodes 74 can be used to determine the position of the positioning electrode 52 relative to the tissue 12. Movement of the positioning electrode 52 proximate the tissue 12 (e.g., within a heart chamber) produces information regarding the geometry of the tissue 12. This information may be used, for example, to generate models and maps of anatomical structures. Information received from the positioning electrode 52 can also be used to display on a display device, such as display device 36, the location and orientation of the positioning electrode 52 and/or the tip of the catheter 18 relative to the tissue 12. Accordingly, among other things, the ECU 34 of the system 32 provides a means for generating display signals used to the control display device 36 and the creation of a graphical user interface (GUI) on the display device 36.

In addition to the above, the ECU 34 may further provide a means for controlling various components of system 28 including, but not limited to, the switch 76. It should be noted that while in an exemplary embodiment the ECU 34 is configured to perform some or all of the functionality described above and below, in another exemplary embodiment, the ECU 34 may be separate and distinct from the system 32, and the system 32 may have another processor (e.g., another ECU) configured to perform some or all of the functionality described herein. In such an embodiment, the processor of the system 32 would be electrically coupled to, and configured for communication with, the ECU 34. However, for purposes of clarity and illustration only, the description below will be limited to an embodiment wherein ECU 34 is part of system 32 and configured to perform the functionality described herein.

The ECU 34 may comprise a programmable microprocessor or microcontroller, or may comprise an application specific integrated circuit (ASIC). The ECU 34 may include a central processing unit (CPU) and an input/output (I/O) interface through which the ECU 34 may receive a plurality of input signals including, for example, signals generated by patch electrodes 74 and the positioning electrode 52 (among others), and generate a plurality of output signals including, for example, those used to control the display device 36 and the switch 76. The ECU 34 may be configured to perform various functions, such as those described in greater detail above and below, with appropriate programming instructions or code (i.e., software). Accordingly, the ECU 34 is programmed with one or more computer programs encoded on a computer-readable storage medium for performing the functionality described herein.

In operation, the ECU 34 generates signals to control the switch 76 to thereby selectively energize the patch electrodes 74. The ECU 34 receives position signals (location information) from the catheter 18 (and particularly the positioning electrode 52) reflecting changes in voltage levels on the positioning electrode 52 and from the non-energized patch electrodes 74. The ECU 34 uses the raw positioning data produced by the patch electrodes 74 and positioning electrode 52 and corrects the data to account for respiration, cardiac activity, and other artifacts using known or hereinafter developed techniques. The corrected data may then be used by the ECU 34 in a number of ways, such as, for example and without limitation, to create a model of an anatomical structure, to map electrophysiological data on an image or model of the tissue 12 generated or acquired by the ECU 34, or to create a representation of the catheter 16 that may be superimposed on a map, model, or image of the tissue 12 generated or acquired by the ECU 34.

Figure 5:
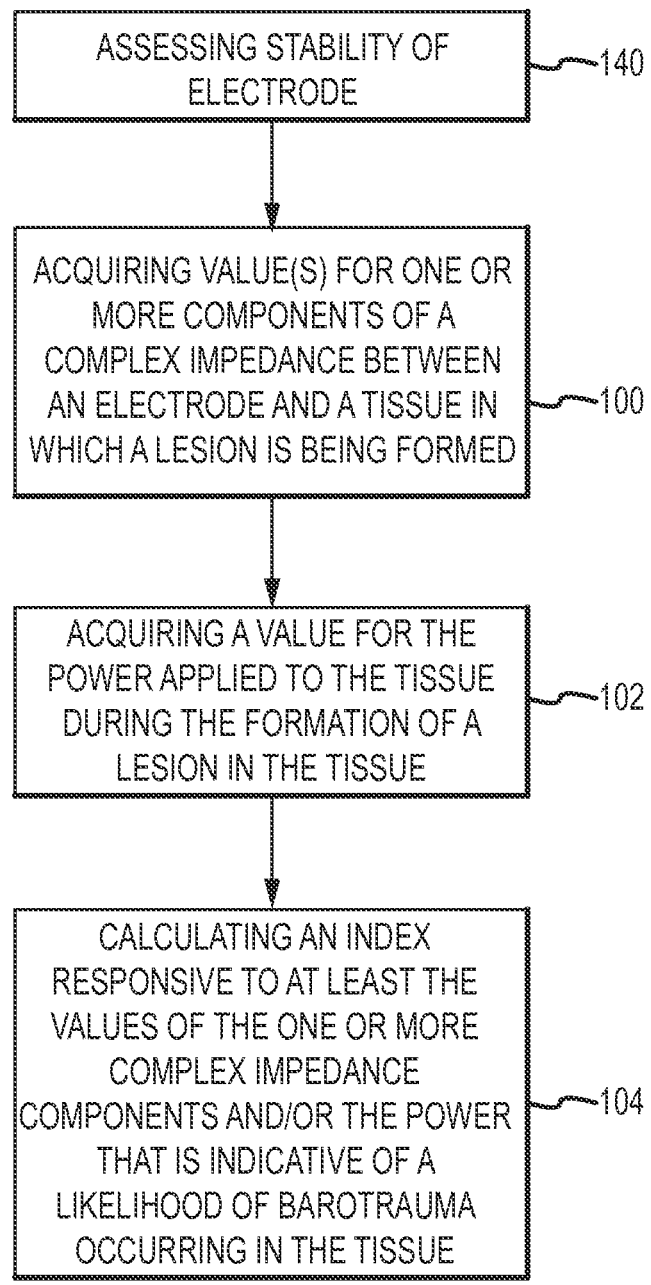
FIG. 5 is flow chart illustrative of an exemplary embodiment of a method for determining the likelihood of barotrauma occurring in tissue during an ablation procedure performed on the tissue in accordance with the present teachings.

With reference to FIG. 5, in an exemplary embodiment, the ECU 34 is further configured to acquire one or more values for one or more components of a complex impedance between the electrode 16 and the tissue 12 (i.e., the resistance (R) and reactance (X), or the impedance magnitude (|Z|) and phase angle ($\phi$), or any combination of the foregoing or derivatives or functional equivalents thereof) (Step 100 in FIG. 5). As will be described in greater detail below, the ECU 34 may acquire these values by receiving them from the complex impedance sensor 64, or by obtaining them from a memory or storage medium associated with, or accessible by, the ECU 34. In an exemplary embodiment, the ECU 34 is configured to calculate an index responsive to at least the value(s) of the one or more components of the complex impedance (Step 104 in FIG. 5), with the index indicative of a likelihood of barotrauma (i.e., endocardial barotrauma) occurring in the tissue 12 as a result of an ablation procedure being performed thereon. In another exemplary embodiment, the ECU 34 is further configured to acquire one or more values for the power or energy applied to the tissue 12 by the ablation generator 26 during the formation of a lesion in the tissue 12 (Step 102 in FIG. 5). In such an embodiment, the ECU 34 is configured to calculate the index responsive to the value(s) of the one or more components of the complex impedance and the value(s) of the applied power. The ECU 34 may be further configured to assess the stability of the catheter 18, and therefore, the electrodes 16, 52, 54 mounted thereon (Step 140). The ECU 34 may then use the stability assessment in the manner as will be described in greater detail below.

Additionally, in an embodiment of the system 10 such as that briefly described above wherein multiple excitation signals are utilized to determine multiple complex impedances, the ECU 34 may be configured to acquire one or more values for components of one or more of the complex impedances for calculating the index. For the sake of clarity and brevity, the following description will be limited to the calculation of the index using a single complex impedance. It should be understood, however, that the present disclosure is not meant to be limited to such an embodiment, but rather includes embodiments wherein components of multiple complex impedances are used in the calculation of the index.

As described above, the ECU 34 preferably comprises a programmable microprocessor or microcontroller, but may alternatively comprise an application specific integrated circuit (ASIC). The ECU 34 may include a central processing unit (CPU) and an input/output (I/O) interface through which the ECU 34 may receive a plurality of input signals including signals from the complex impedance sensor 64 of the tissue sensing circuit 28 (for the value(s) of the complex impedance component(s)) and the ablation generator 26 or another recording system in communication with the ablation generator 26 (for the power level) (in addition to those described above); and to generate a plurality of output signals.

In accordance with one aspect of the present disclosure, the ECU 34 may be programmed with a computer program (i.e., software) encoded on a computer-readable storage medium for determining a likelihood of barotrauma occurring in the tissue 12 during the formation of a lesion therein as a result of an ablation procedure being performed thereon. As illustrated in FIG. 5, and generally speaking, the program includes code for calculating an index responsive to values for one or more components of the complex impedance between the electrode 16 and the tissue 12 and, in an exemplary embodiment, the value(s) of the power or energy applied to the tissue 12 through the electrode 16, with the index indicative of a likelihood of barotrauma occurring in the tissue 12. The program further includes code for performing or carrying out some or all of the functionality of the ECU 34 described in greater detail below.

Experimentation and analysis were performed to determine an equation based at least in part on complex impedance that could be used by the ECU 34 to predict the likelihood of endocardial barotrauma occurring in tissue during lesion formation therein (i.e., an equation used to calculate an index that is indicative of the likelihood of barotrauma occurring in the tissue). Using controlled experimentation and a binary logistic regression model performed using software sold under the registered trademark "MINITAB" by Minitab, Inc., an endocardial barotrauma prediction algorithm/equation was derived corresponding to the particular equipment and arrangement of the system 10 used in the experimentation and analysis. Factors that were evaluated in the testing and analysis included, but were not necessarily limited to, resistance (R), reactance (X), magnitude of impedance (Z), electrical coupling index (ECI), and phase angle ($\phi$) prior to the onset of lesion formation in the tissue; the R, X, Z, ECI, and $\phi$ at the start of lesion formation; the magnitude of change in, or slope of, R, X, Z, ECI, and $\phi$ from the start of lesion formation, or at some point in time after the start of lesion formation, to the end of lesion formation or to a point in time subsequent to the start of lesion formation and prior to the end of lesion formation; the maximum rate of change for R, X, Z, ECI, and $\phi$ from the start of lesion formation to the end of lesion formation; the mean RF power applied to the tissue during lesion formation; RF duration; the natural log of RF duration; the product of the RF power and the RF duration; and electrical current. A binary regression model including all factors was created first, and then certain factors were eliminated. After the elimination of a factor, the model was re-run, and the process was repeated.

Once this process was completed, it was generally determined that in one exemplary embodiment, and for the particular equipment and arrangement of the system 10 used in the experimentation and analysis, the resistance (R) and reactance (X) components of the complex impedance between the electrode 16 and the tissue 12, and the power applied to the tissue 12 were preferred factors to be considered in the algorithm. More specifically, it was determined that the changes in resistance (dR) and reactance (dX) from the start of the formation of a lesion to a subsequent point in time in the formation process of the same lesion, the change in resistance (dR) divided by the change in time (dt) from the start of the lesion formation process to the point in time the index is being calculated (dR/dt), and an electrical current value calculated by taking the square root of the quotient of the division of the mean value of the RF power applied to the tissue 12 from the start of the lesion formation process to the point in time the index is being calculated by the value of the resistance ($R_0$) between the electrode 16 and the tissue 12 just prior to the start or onset of the lesion formation process $$\left(\text{i.e.,}\ \sqrt{\frac{MeanPower}{R_0}}\right)$$

were the most significant factors to be considered in the context of the equipment used for testing.

It was further determined that various other factors would possibly have an impact on the accuracy of the prediction algorithm. These factors include, for example and without limitation, certain parameters and/or characteristics of the equipment and/or arrangement of the system 10 (such as, for example, the type of catheter and ablation generator being used, the irrigation flow rate, etc.).

Accordingly, it was determined that the most computationally efficient index would be based on the "electrical" factors above (i.e., resistance, reactance, power values, etc.), as well as certain predetermined coefficients and constants to account for design parameters or characteristics of the devices/equipment used in the ablation procedure. More specifically, it was determined that the best equation or algorithm was the equation (3):

$$\text{Index} = a + b_1 * \frac{dR}{dt} + b_2 * I + b_3 * dR + b_4 * dX \qquad (3)$$

In this equation, the constant a and the coefficients $b_1$-$b_4$ are predetermined values that are intended to account for the various factors associated with, for example, the equipment used in the ablation procedure (i.e., type of catheter and/or ablation generator, irrigation flow rate, etc.). The constant and coefficients can be determined in a number of ways, such as, for example, controlled experimentation or using analyses, such as, for example, a regression analysis. Once the constant and coefficients are determined, they may be stored or programmed into the ECU 34, or a memory/storage device 80 (best shown in FIG. 1) associated therewith or accessible thereby. Alternatively, the catheter 18 may itself include a memory such as an EEPROM that stores numerical values for the coefficients/constant corresponding to that particular type of catheter and/or other equipment of the system 10, or stores a memory address for accessing the numerical values in another memory location. The ECU 34 may retrieve these values or addresses directly or indirectly and factor them into the index calculation accordingly.

It should be understood that while the coefficients and constant of the particular equation above may vary depending on, among other things, the specific catheter used, the ablation generator employed, the irrigation flow rate, and potentially the patient, other equipment in the system, the species being treated, and the like, the index calculated using the particular equation above will always be responsive to both components of the complex impedance and the RF power applied to the tissue in order to arrive at an optimal assessment of the likelihood or predictability of barotrauma occurring in the tissue 12 during an ablation procedure performed thereon.

By way of example and illustration, employing the experimental testing and regression analysis described above, and using a 4 mm open irrigated RF ablation catheter available from St. Jude Medical, Inc. under the name "Cool Path" and an IBI-1500T-11 RF Cardiac Ablation Generator available from Irvine Biomedical, Inc., the best prediction of endocardial barotrauma for a system employing those particular components was determined to be the following equation (4):

$$\text{Index} = -16.4174 + 2.20852 * \frac{dR}{dt} + \qquad (4)$$
$$0.0191087 * I + 0.0822815 * dR + 0.622496 * dX$$

This was determined by creating temperature controlled ablation lesions (20-50 Watts, 40-50° C., 5-60 seconds, n=318) on the endocardial surface of explanted bovine atria and ventricles in either parallel or perpendicular orientation. Data was collected and a binary regression model was performed to come to equation (4), and the values of the constant and coefficients thereof. The solution to the equation represents the natural log of the odds for a barotrauma to occur. As will be described in greater detail below, in an exemplary embodiment, the user of the system 10 is alerted to an increased chance or likelihood of barotrauma occurrence if the calculated index exceeds a predetermined threshold. For equation (4), this threshold was determined to be −2.5. When validation testing was performed using equation (4) and a threshold of −2.5, all of the lesions resulting in barotrauma were correctly categorized as positive events (i.e., when barotrauma was predicted to occur, it occurred), and 82% of lesions that did not result in barotrauma were correctly categorized negative events. Accordingly, the efficacy of the equation was confirmed/validated.

It should be noted that although the equations above and the corresponding description above and below focus on the rectangular coordinates of resistance (R) and reactance (X), it should be understood that the index may also be based on values associated with the polar coordinates of impedance magnitude (|Z|) and phase angle (φ), or indeed any combination of the foregoing components of the complex impedance and derivatives or functional equivalents thereof. For example, in addition to the values of the constant and coefficients of the index equation above changing due to factors such as the type of catheter, the type of ablation generator, and other characteristics or parameters, these factors may also determine or impact which component or components of the complex impedance and/or aspects of the power are the most significant, and therefore, best for use in the equation for calculating the index for certain equipment.

For instance, depending on the catheter and/or other equipment used, it may be determined, using the experimentation and analysis set forth above, that (dφ/dt) is more predictive than (dR/dt), or that perhaps dZ is more significant than either dR or dX. It may also be determined that the values of the components taken or measured at certain points in time (i.e., prior to the onset of lesion formation, at the start of lesion formation, etc.) are more predictive or significant than the values of those components or other components taken at a different time. Further, while the equations set forth above are based on two components of the complex impedance (e.g., R and X), in other exemplary embodiments the equation may be based on a single component (as will be illustrated below), or more than two components of the complex impedance, and may include more or less terms than equations (3) and (4) above. Additionally, while the equations (3) and (4) include a term based on the mean value of the power applied to the tissue (i.e., the electrical current (I)), in other embodiments one or more other aspects of the RF power, such as, for example, the natural log of the RF power, the RF duration, the product of the RF duration and a value of RF power, and the like, may be used in addition to or instead of the mean power value. Accordingly, in certain instances the value of the electrical current (I) based in part on the mean power value may or may not be used in calculating the index. Therefore, it will be appreciated that the form of the equation to be used for calculating the index may be highly dependent on the type or types of the equipment used in the ablation procedure. Therefore, the present disclosure is not meant to be limited to the use of any particular complex impedance components, particular aspects of the RF power, or number of components.

Rather, equations used to calculate the index that are based on one or more values of one or more components of one or more complex impedances, and/or one or more values of aspects of the power applied to the tissue 12 remain within the spirit and scope of the present disclosure.

Once the particular complex impedance components to be used in calculating the index for a particular catheter or arrangement of the system 10 are determined and the form of the equation is resolved, the components of the complex impedance (or an indication corresponding thereto), the equation to be used, and/or the specific terms of the equation (including, if appropriate, the constant(s) and/or coefficients for the equation terms) may be stored or programmed into the ECU 34, or a memory/storage medium 80 (best shown in FIG. 1) associated therewith or accessible thereby. Alternatively, the catheter 18 or another component in the system 10 may include a memory, such as an EEPROM, that is configured to store the above identified information or a memory address for accessing the information stored in another memory location corresponding to that particular type of catheter and/or other equipment of the system 10. The ECU 34 may retrieve this information or addresses directly or indirectly and use it to calculate the index.

Figure 6:
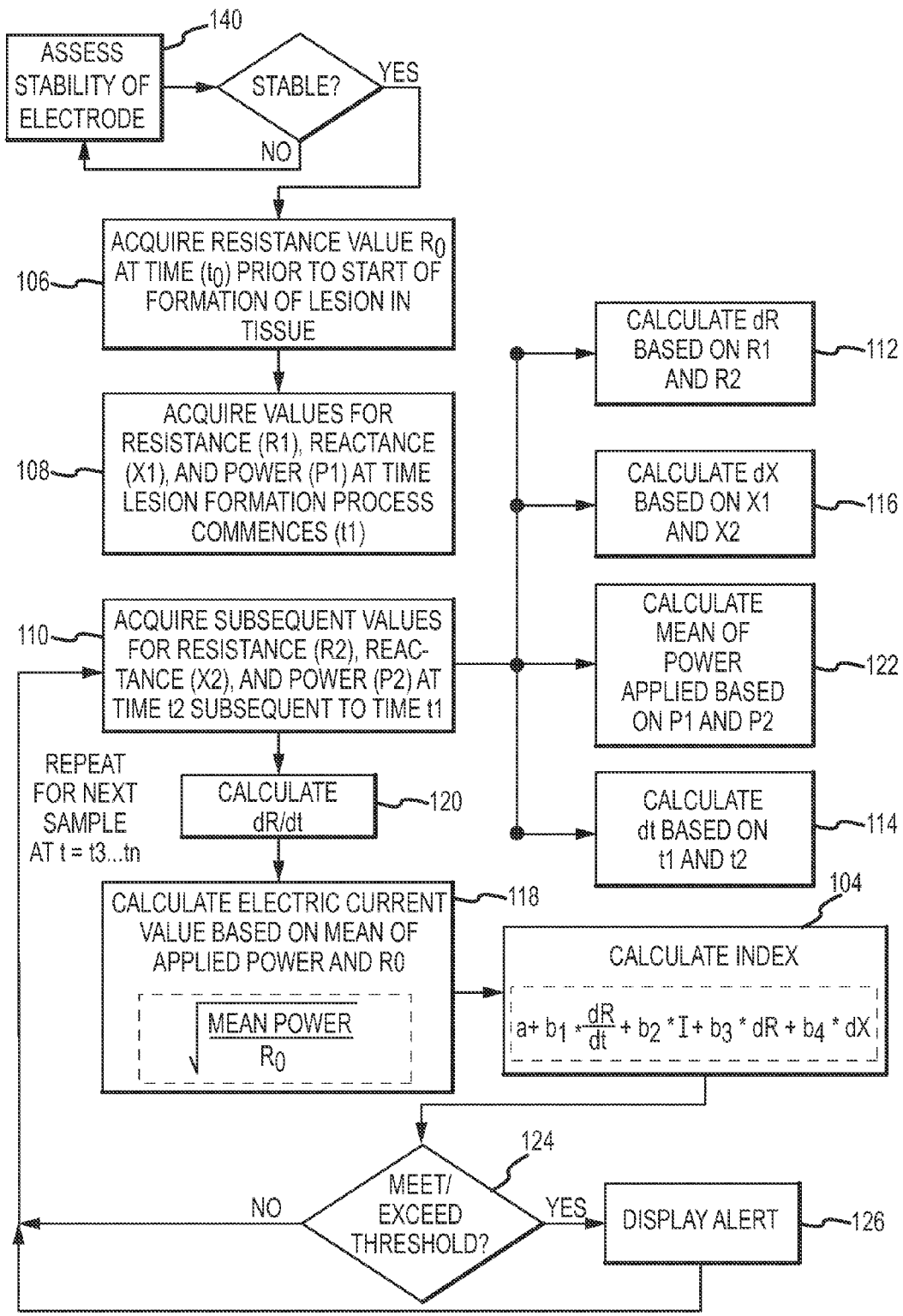
FIGS. 6 and 7 are flow charts illustrative of alternate embodiments of the methodology illustrated in FIG. 5 shown in greater detail.
Figure 7:
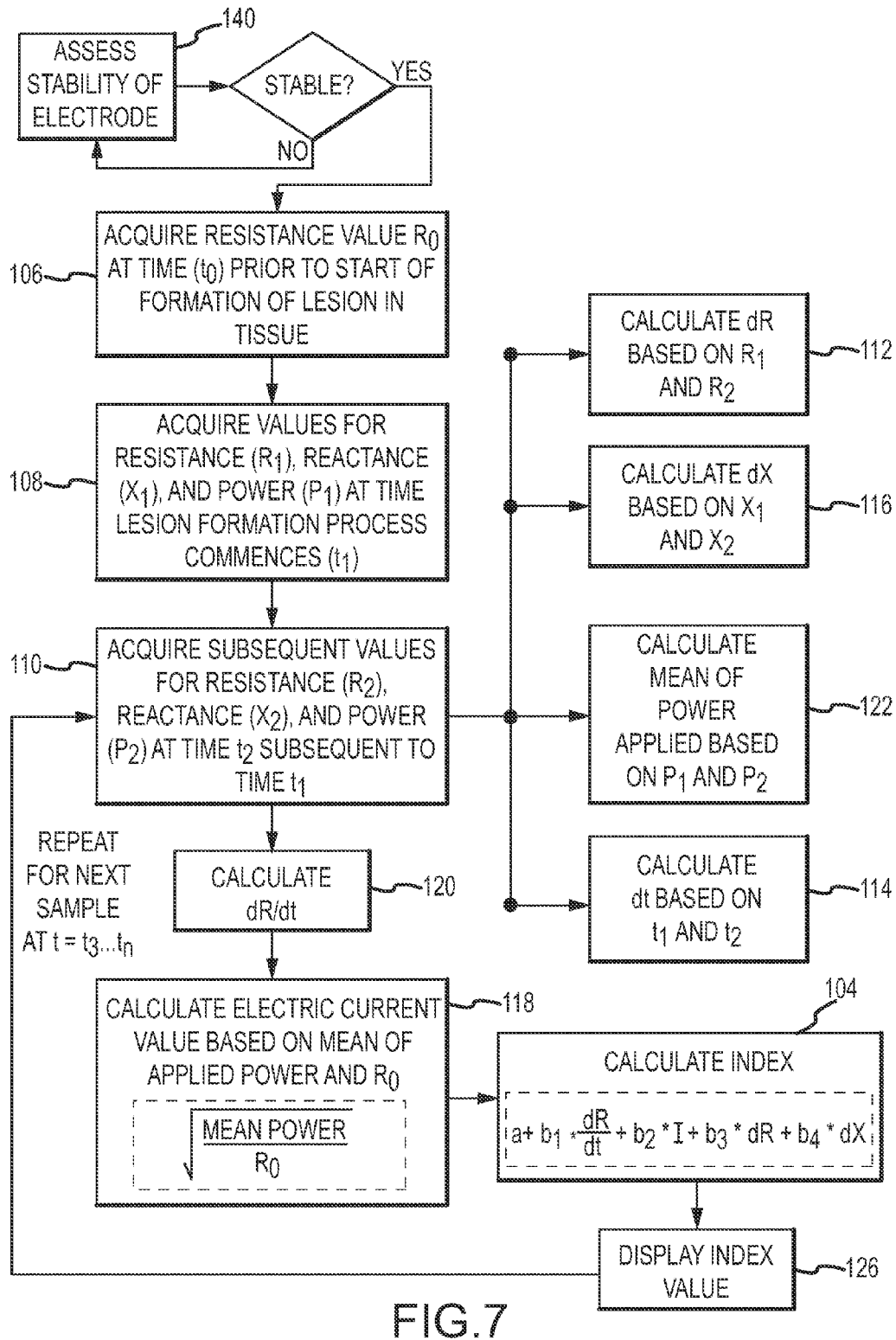

With reference to FIGS. 5-7, an exemplary index calculation will now be described. In this example, the index is calculated based, in part, on two components of the complex impedance, namely, resistance and reactance, and a mean value of the power applied to the tissue (i.e., using the equation (3) above). It will be appreciated in view of the above, however, that the present disclosure is not meant to be limited to such an exemplary calculation.

In addition to being configured to calculate the index described above, the ECU 34 is also configured to acquire and/or calculate the terms used in the equation for calculating the index (i.e., dR, dt, I, dX, etc.). As described above, and as illustrated in FIG. 5, in this embodiment, the ECU 34 is configured to acquire values for the first and second components of the complex impedance (i.e., R and X) (Step 100 in FIG. 5) and the value of power being applied to the tissue 12 during the ablation procedure (Step 102 in FIG. 5). More particularly, with reference to FIGS. 6 and 7, the ECU 34 is configured to acquire a value for the resistance $R^0$ between the electrode 16 and the tissue 12 at a point in time $t_0$ just before the start of an ablation procedure performed on the tissue 12 (Step 106 in FIGS. 6 and 7). This value may be received from the complex impedance sensor 64, and may be stored along with the corresponding time ($t_0$) in a temporary or permanent memory or storage medium that is either part of, or accessible by, the ECU 34, such as, for example, the memory 80.

The ECU 34 is further configured to acquire values for R, X, and RF power applied to the tissue 12 (P) at a point in time $t_1$ at which a process for forming a lesion in the tissue 12 begins ($R_1$, $X_1$, $P_1$) (Step 108 in FIGS. 6 and 7). The R and X values may be received from the complex impedance sensor 64, and the power value may be received from the ablation generator 26, or a reporting system associated therewith, and then each value may be stored along with the corresponding time (i.e., $t_1$) in a table of a memory or storage medium, such as that described above, in the manner illustrated, for example, in FIG. 8.

The ECU 34 is further configured to sample the values for R, X, and P throughout the formation of the lesion at one or more respective predetermined sampling rates in order to constantly and continuously monitor the likelihood of barotrauma occurring in the tissue 12 (See, for example, Step 110 in FIGS. 6 and 7). For example, and without limitation, the sampling rate used in the experimentation relating to equation (4) described above was 2048 times per second. However, a sampling rate on the order of 100 to 800 times per second would also suffice, and therefore, the present disclosure is not meant to be limited to any one particular sampling rate. Accordingly, the ECU 34 is configured to sample the signal received from the complex impedance sensor 64 at a predetermined rate and to store the corresponding R and X values (i.e., $R_2$, $R_3$, ..., $R_n$ and $X_2$, $X_3$, ..., $X_n$) derived therefrom in the memory or storage medium described above along with the corresponding times (i.e, $t_2$, $t_3$, ..., $t_n$) at which the values were sampled (See FIG. 8). Similarly, the ECU 34 is configured to sample the signal received from the ablation generator 26, or an associated reporting system, at a predetermined rate and to store the corresponding power values (i.e., $P_2$, $P_3$, ..., $P_n$) in a memory such as that described above along with the corresponding times (i.e., $t_2$, $t_3$, ..., $t_n$) at which the samples were taken (See FIG. 8).

In an exemplary embodiment, after each value of R, X, and P is sampled, the system 10 is configured to calculate the index described above. Alternatively, rather than calculating the index after each sample, the ECU 34 may be configured to calculate the index at some other rate such as after a certain number of samples have been collected or after a certain amount of time has elapsed. For the purposes of clarity and brevity alone, the description below will be directed to an embodiment wherein the index is calculated after a sample of each of the R, X, and P is collected at a particular point in time. It will be appreciated, however that the present disclosure is not meant to be limited to such an embodiment.

After a sample of each of R, X, and P are collected, the ECU 34 is configured to perform a number of calculations. For example, and as illustrated in FIGS. 6 and 7, the ECU 34 is configured to calculate a change in the resistance (dR) (Step 112), a change in the time, or the elapsed time, represented by the time interval from the point in time that the lesion formation process commenced to the point in time that the current value was sampled (dt) (Step 114), a change in the reactance (dX) (Step 116), and an electrical current value (I) based, in part, on the mean of the power applied during the lesion formation process and the resistance $R_0$ between the electrode 16 and the tissue 12 prior to the start of the lesion formation process (i.e., prior to the commencement of the ablation procedure) (Step 118).

With respect to the change in resistance, the ECU 34 is configured to calculate the change in resistance over the time interval beginning at the point in time at which the lesion process commenced ($t_1$), to the point in the time at which the current resistance value was sampled. Therefore, with reference to FIGS. 6 and 7, if the index is being calculated using the values sampled at time $t_2$, the change in resistance is calculated by subtracting the resistance $R_2$ from the resistance $R_1$. Accordingly, the ECU 34 is configured to acquire resistance values $R_1$ and $R_2$ (from the memory 80, for example) and to perform the calculation to determine the change in resistance. Similarly, if the index is being calculated at time $t_3$, the change in resistance is calculated by subtracting the resistance $R_3$ from the resistance $R_1$, and so on and so forth. Accordingly, regardless of the point in time of the lesion formation process at which the index is being calculated, the current resistance value is processed with resistance value $R_1$ to determine the change in resistance.

With respect to the change in time, the ECU 34 is configured to calculate the change in time or the elapsed time represented by the time interval from the point in time that the lesion formation process commenced (time $t_1$) to the point in time that the current values were sampled, and therefore, the point in time that the index is being calculated. Accordingly, if the index is being calculated using the values sampled at time $t_2$, the change in time is calculated by subtracting the time $t_1$ from the time $t_2$ to determine the elapsed time of the procedure thus far. Accordingly, the ECU 34 is configured to acquire the times corresponding to $t_1$ and $t_2$ and to perform the calculation to determine the change in time or the amount of elapsed time. Similarly, if the index is being calculated at time $t_3$, the change in time is calculated by subtracting the time $t_1$ from the time $t_3$, and so on and so forth. Accordingly, regardless of the point in time of the lesion formation process at which the index is being calculated, the current time value is always processed with the time value $t_1$ to determine the change in time.

Once the change in resistance (dR) and the change in time (dt) are calculated, the ECU 34 is configured to calculate the (dR/dt) term in the index equation (Step 120). Accordingly, if the index is being calculated using the values sampled at time $t_2$, (dR/dt) is calculated by dividing the change in the resistance over the time interval between $t_1$ and $t_2$ ($dR_{1-2}$) by the change in time represented by the time interval $t_1$-$t_2$ ($dt_{1-2}$). Similarly, if the index is being calculated at time $t_3$, (dR/dt) is calculated by dividing the change in the resistance over the time interval between $t_1$ and $t_3$ ($dR_{1-3}$) by the change in time represented by the time interval $t_1$-$t_3$ ($dt_{1-3}$), and so on and so forth. Accordingly, the ECU 34 is configured to calculate the change in resistance and the change in time, and to then divide the change in resistance by the change in time.

With respect to the change in reactance, the ECU 34 is configured to calculate the change in reactance over the time interval beginning at the point in time that the lesion process commenced (time $t_1$), to the point in the time corresponding to the current reactance value. Therefore, if the index is being calculated using the values sampled at time $t_2$, the change in reactance is calculated by subtracting the reactance $X_2$ from the reactance $X_1$. Accordingly, the ECU 34 is configured to acquire reactance values $X_1$ and $X_2$ and to perform the calculation to determine the change in reactance. Similarly, if the index is being calculated at time $t_3$, the change in reactance is calculated by subtracting the reactance $X_3$ from the reactance $X_1$, and so on and so forth. Accordingly, regardless of the point in time of the lesion formation process at which the index is being calculated, the current reactance value is processed with reactance value $X_1$ to determine the change in reactance.

With respect to the electrical current value (I), the ECU 34 is configured to first calculate a mean value for the RF power applied to the tissue 12 over the time interval beginning at the point in time that the lesion process commenced ($t_1$), to the point in the time corresponding to the current power value (Step 122). Therefore, if the index is being calculated using the values sampled at time $t_2$, the mean value of the power is calculated using the power value samples $P_1$ and $P_2$. Similarly, if the index is being calculated using the values sampled at time $t_3$, the mean value of the power is calculated using the power value samples $P_1$, $P_2$, and $P_3$, and so on and so forth. Accordingly, the ECU 34 is configured to acquire the appropriate power values and to perform the calculation to determine the mean value of the applied power ("MeanPower"). In an exemplary embodiment, a smoothing technique, such as, for example, an exponential moving average, a median filter, or some other known technique, may be used to account for the changes in impedance. Once the MeanPower is calculated, the ECU 34 is configured to calculate the electrical current value (I) using equation (5):

$$I = \sqrt{\frac{MeanPower}{R_0}} \qquad (5)$$

Accordingly, the mean value of the power applied to the tissue 12 up until the point in time the index is calculated is divided by, in an exemplary embodiment, the resistance value $R_0$ corresponding to the point in time just before the lesion formation process commenced. Alternatively, in another exemplary embodiment, it may be determined that the electrical current value is more accurately calculated by dividing the mean value of the power by a resistance value such as, for example, $R_1$. Accordingly, the present disclosure is not limited to the use of any one particular resistance value in calculating the electrical current value.

Once all of the terms above are calculated, the ECU 34 is configured and able to calculate the index in order to determine the likelihood of barotrauma occurring in the tissue at that point in time (Step 104). Accordingly, the ECU 34 is configured to acquire the correct or appropriate values for the constant a and the coefficients $b_1$-$b_4$, and, using the appropriate index equation, to process these values with the values described above to come to an index value. Accordingly, the computer program stored on or accessible by the ECU 34 includes code for carrying out the execution of the index equation. Once the index value is calculated, it may be used in a number of ways.

In an exemplary embodiment, such as that illustrated in FIG. 6, the system 10, and the ECU 34, in particular, is programmed with, or configured to access, an index threshold value corresponding to a barotrauma threshold. In one embodiment, the threshold may be the minimum index value at which barotrauma occurs. Alternatively, the threshold may be the maximum index value at which barotrauma will not occur. In either instance the threshold value is determined by experimentation and/or analysis performed prior to use of the system 10 (i.e., as part of the manufacturing or set up process, for example), and may be impacted by the factors described above, such as, for example, the type of catheter, the type of ablation generator, and other characteristics relating, for example, the equipment of the system 10. In such an embodiment, the calculated index is compared to the threshold value (Step 124) and, based on that comparison, an indication may be provided to the user that there is an increased chance or likelihood of a barotrauma occurring in the tissue (Step 126) (e.g., if the index meets or exceeds the threshold value). An indication may also be provided to the user that a barotrauma is not likely to be caused in the tissue (e.g., if the index falls below the threshold value).

Take, for example, equation (4) above, and the corresponding threshold of −2.5. If this equation and threshold are used, and a calculated index has a value that is greater than −2.5 (i.e., less negative/more positive), an indication may be provided to the user that there is an increased likelihood that a barotrauma will occur. Alternatively, if the index has a value less than −2.5 (i.e., more negative/less positive), an indication may or may not be provided to the user that there is little risk or likelihood of a barotrauma occurring in the tissue 12. In an exemplary embodiment this threshold value is set prior to the system 10 being used and is not adjustable. Alternatively, in another exemplary embodiment the threshold may be adjustable by the user to change the sensitivity of the system. In the latter embodiment, the system 10 may include a user interface 82, such as, for example, a touch screen, a keyboard, a keypad, a slider control, or some other user-controllable input device that is electrically connected to the ECU 34 to allow the user to adjust the threshold value, and therefore, the sensitivity of the system 10.

Alternatively, as illustrated in FIG. 7, rather than comparing the calculated index to a threshold value, in another exemplary embodiment, the index value may be displayed (Step 126 in FIG. 7) for the user to see and to react to, if necessary; or may be used in conjunction with a look-up table stored on, or accessible by, the ECU 34 to determine whether the index value is such that a warning should be provided to the user. Accordingly, the calculated index may be used and/or evaluated in any number of ways.

In another exemplary embodiment, rather than calculating the index based on values of one or more components of the complex impedance between the electrode 16 and the tissue 12, and value(s) of the power applied to the tissue 12, the index is calculated based on values for a single component of the complex impedance. For example, during experimentation it was determined that for at least the equipment being used and the particular arrangement of the system 10, a decrease in the reactance between the electrode 16 and the tissue 12 during an ablation procedure performed on the tissue 12 was indicative of a risk or likelihood of barotrauma occurring in the tissue 12. More particularly, as will be described in greater detail below, in one embodiment, the ECU 34 is configured to calculate the index based on two or more values of the reactance (X) between the electrode 16 and the tissue 12 sampled at two or more points in time during the lesion formation process. It will be appreciated that while the description below is directed to the calculation of the index based solely on the reactance component of the complex impedance, in other embodiments components of the complex impedance other than reactance may be used to calculate the index. Therefore, the description below is provided for exemplary purposes only and is not meant to be limiting in nature.

Figure 9:
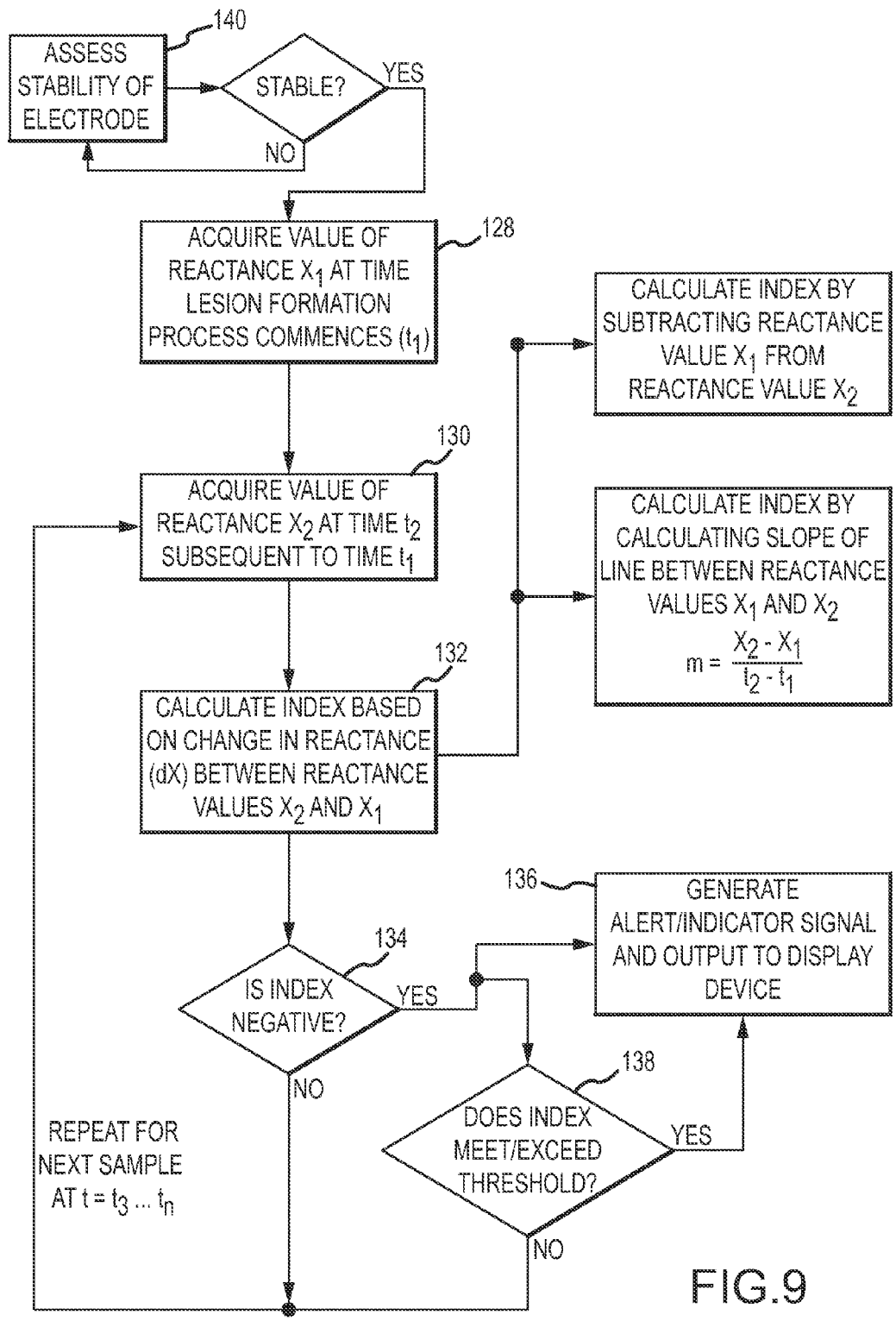
FIGS. 9 and 10 are flow charts illustrative of alternate embodiments of the methodology illustrated in FIG. 5 shown in greater detail.
Figure 10:
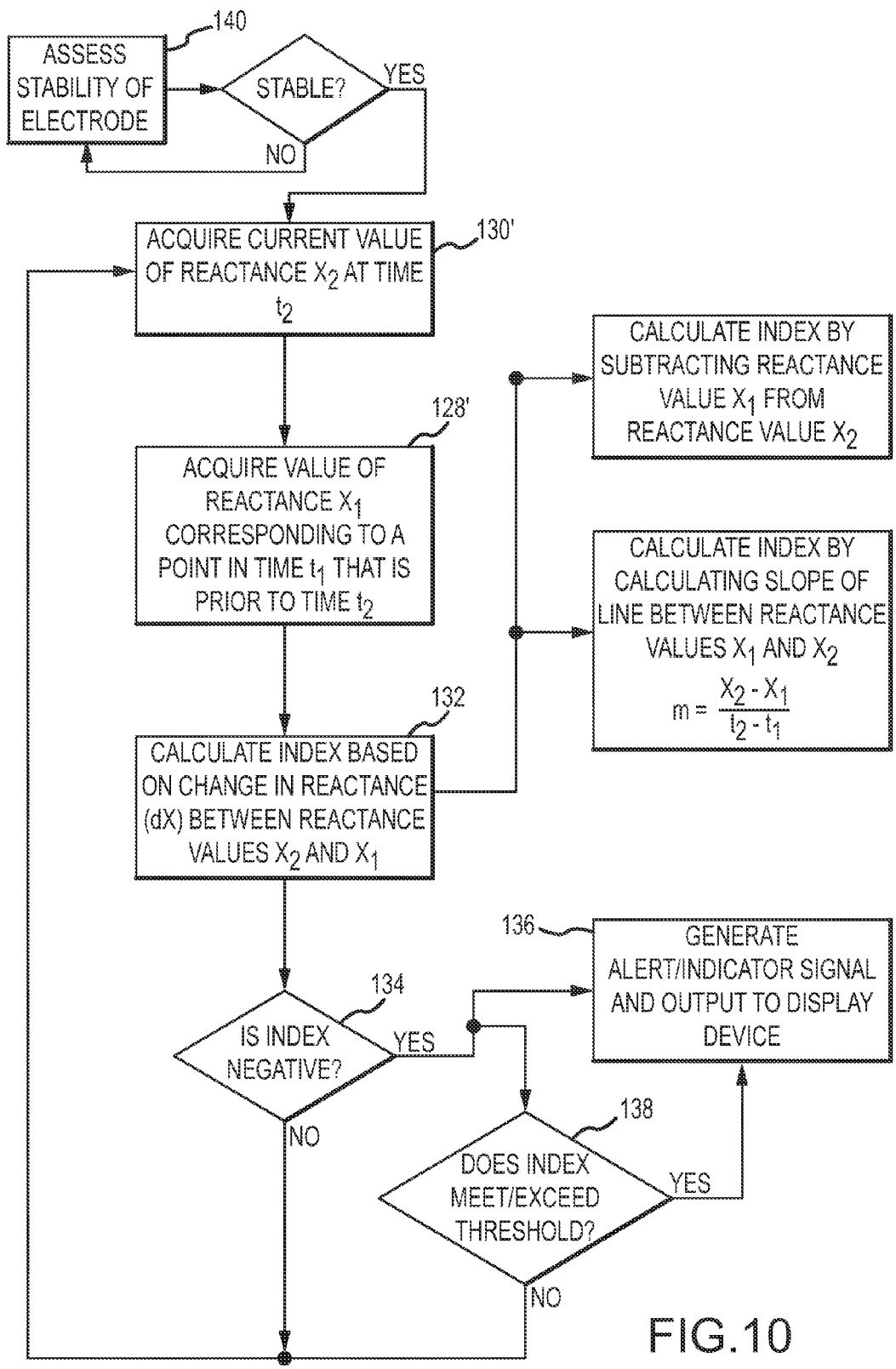

Accordingly, with reference to FIGS. 9 and 10, in an exemplary embodiment, the ECU 34 is configured to acquire a plurality of values for the reactance component of the complex impedance corresponding to a plurality of points in time. These values may be received from the complex impedance sensor 64, or may be obtained from a memory or storage medium that is part of or accessible by the ECU 34. The ECU 34 is further configured to calculate a change in reactance (dX) between two or more of the plurality of reactance values, and to calculate the index based on the change in reactance (dX).

In one exemplary embodiment, the index equals the change in reactance (dX) over a time interval. In one embodiment illustrated, for example, in FIG. 9, the reactance values used to calculate dX, and therefore, the index, are the values at the time the lesion formation process commences (i.e., time $t_1$), and a point in time subsequent to the commencement of the lesion formation process (i.e., time $t_2, t_3, \ldots t_n$) (thus, in this embodiment, the reactance value at the time the lesion formation process commences is always used in the index calculation). Accordingly, the ECU 34 is configured to acquire the value of the reactance $X_1$ at time $t_1$ just after the lesion formation process commences, which may be stored in a memory or other storage medium, such as, for example, that described above and illustrated in FIG. 8 (Step 128). The ECU 34 is further configured to acquire values of the reactance (i.e., $X_2, X_3, \ldots, X_n$) at times subsequent to time $t_1$ (i.e., time $t_2, t_3, \ldots, t_n$) (Step 130). As with the reactance $X_1$, the ECU 34 may be configured to store each reactance value in a memory or storage device along with its corresponding time value. Accordingly, the ECU 34 is configured to sample the value of the reactance between the electrode 16 and the tissue 12 at a predetermined rate following the commencement of the lesion formation process. The description of sampling rates set forth above applies here with equal force, and therefore, will not be repeated.

As described above, the ECU 34 is configured to calculate the change in the reactance over a time interval defined by, for example, the start of the lesion formation process and a point in time subsequent thereto at which the likelihood of barotrauma occurrence is to be evaluated (Step 132). The ECU 34 may calculate the change in reactance for each reactance value sampled, or may calculate the change in reactance after a certain number of reactance value samples are collected or after a certain amount of time has elapsed. For ease of description purposes, however, the description below will be limited to an embodiment wherein the change in reactance is calculated after each reactance value sample is collected. It will be appreciated in view of the above, however, that the present disclosure is not limited to such an embodiment.

Accordingly, with continued reference to FIG. 9, once the ECU 34 acquires (from the memory 80, for example) a reactance value $X_1$ corresponding to the commencement of the lesion formation process (time $t_1$), and a reactance value $X_2$ (from either the complex impedance sensor 64 or the memory 80, for example) corresponding to a point in time subsequent to time $t_1$ (i.e., time $t_2$), the ECU 34 is configured to calculate the change in reactance between reactance value $X_2$ and reactance value $X_1$. As illustrated in FIG. 9, in an exemplary embodiment, the ECU 34 is configured to subtract $X_1$ from $X_2$ to calculate the index.

Once the index is calculated, the value itself may be displayed for the user to see and interpret in the same manner as described elsewhere herein, or the ECU 34 may be configured to evaluate or process the index to determine whether there is a likelihood of barotrauma occurring in the tissue 12 (Step 134). More particularly, in an exemplary embodiment, the ECU 34 is configured to determine whether the change value is a positive or a negative value. In an exemplary embodiment, if the value is positive, then the ECU 34 can determine that there has not been a decrease in the reactance, and therefore, there is currently no risk or likelihood of barotrauma occurring in the tissue 12. In such an instance, the ECU 34 may or may not provide the user of the system 10 with an indication of this determination. The ECU 34 may then repeat the process for the next reactance value sample corresponding to a subsequent point in time (e.g., time $t_3$), and so on and so forth. If, however, the change value is negative, the ECU 34 can determine that the reactance has decreased, and therefore, there is a risk or likelihood of barotrauma occurring in the tissue 12. The ECU 34 may then, as is described elsewhere herein, provide the user with an alert or some other indicator to advise the user of the likelihood of barotrauma occurring so that the user may take corrective or preventative action. Additionally, or in the alternative, the ECU 34 may cause the value of the index to be displayed for the user to see and interpret.

With reference to FIG. 10, in another exemplary embodiment, rather than always calculating the change in the reactance based on the reactance value at the commencement of the lesion formation process and the reactance value sampled at a time subsequent thereto, the ECU 34 is configured to calculate the change in reactance, and therefore the index, based on a current reactance value (e.g., $X_2$) (i.e., a reactance value between the electrode 16 and the tissue 12 at the time of the calculation, or a previously received reactance value (e.g., $X_1$) sampled more recently than the other reactance value (e.g., $X_1$) being taken into account) and a prior reactance value (e.g., $X_1$) sampled at a point in time after the start of the lesion formation process but before the sampling of the reactance value (e.g., $X_2$) (accordingly, the prior reactance value may be the reactance value at the commencement of the lesion formation process, or may be a value corresponding to point in time subsequent thereto). In such an embodiment, and as described above, the ECU 34 is configured to sample the value of the reactance between the electrode 16 and the tissue 12 at a predetermined rate, and to store each sampled value in a memory or storage device described elsewhere herein. As with the embodiment described above and illustrated in FIG. 9, the ECU 34 may calculate the change in reactance for each reactance value sampled, or may calculate the change in reactance after a certain number of reactance value samples have been collected or after a certain amount of time has elapsed. For ease of description purposes, however, the description below will be limited to an embodiment wherein the change in reactance is calculated after each reactance value sample is collected. It will be appreciated in view of the above, however, that the present disclosure is not limited to such an embodiment.

Accordingly, with continued reference to FIG. 10, the ECU 34 is configured to acquire (from the complex impedance sensor 64 or the memory 73, for example) a current reactance value $X_2$ (Step 130'). The ECU 34 is configured to then acquire (from the memory 80, for example) a reactance value $X_1$ sampled prior to the time at which the reactance value $X_2$ was sampled (Step 128'). The prior reactance value $X_1$ may be the most immediate prior reactance value to the current reactance value $X_2$, or may be another prior reactance value chosen based on certain criteria (e.g., a value acquired a certain amount of time prior to the current time, a value acquired a certain number of collected samples prior, etc.). In any event, once the ECU 34 has acquired the current and prior reactance values, it is configured to calculate the change in reactance, and therefore, the index (Step 132), and to evaluate/process the index (Step 134), in the same manner described above with respect to FIG. 7. Accordingly, this description will not be repeated here.

With continued reference to FIGS. 9 and 10, in another exemplary embodiment, rather than calculating the index based on the change in the reactance alone, the index is calculated by calculating the slope of a line between two reactance values corresponding to two different points in time (i.e., index=slope). As with the embodiment described above, in one exemplary embodiment illustrated, for example, in FIG. 9, the reactance values used to calculate the slope, and therefore, the index, are the values at the time the lesion formation process commences (i.e., time $t_1$), and a point in time subsequent to the commencement of the lesion formation process (i.e., time $t_2, t_3, \ldots, t_n$) (thus, in this embodiment, the reactance value at the commencement of the lesion formation process is always used in the slope, and therefore, index, calculation). Accordingly, the ECU 34 is configured to acquire the value of the reactance $X_1$ corresponding to time $t_1$ just after the commencement of the lesion formation process, which may be stored in a memory or some other storage medium, such as, for example, that described above and illustrated in FIG. 8 (Step 128). The ECU 34 is further configured to acquire values of the reactance (i.e., $X_2, X_3, \ldots, X_n$) at times subsequent to time $t_1$ (i.e., time $t_2, t_3, \ldots, t_n$) (Step 130). As with the reactance value $X_1$, the ECU 34 may be configured to store each reactance value in a memory or storage medium along with its corresponding time. Accordingly, the ECU 34 is configured to sample the value of the reactance between the electrode 16 and the tissue 12 at a predetermined rate following the commencement of the lesion formation process. The description of sampling rates set forth above applies here with equal weight, and therefore, it will not be repeated here.

As briefly described above, the ECU 34 is configured to calculate the slope of the line between a reactance value at the commencement of the lesion formation process, and a reactance value at a point in time subsequent thereto (Step 132). The ECU 34 may calculate the slope for each reactance value sampled, or may calculate the slope after a certain number of reactance value samples have been collected or after a certain amount of time has elapsed. For ease of description purposes, however, the description below will be limited to an embodiment wherein the slope is calculated after each reactance value sample is collected. It will be appreciated in view of the above, however, that the present disclosure is not limited to such an embodiment.

Accordingly, with continued reference to FIG. 9, once the ECU 34 acquires (from the memory 80, for example) a reactance value $X_1$ corresponding to the commencement of the lesion formation process (i.e., time $t_1$), and a reactance value $X_2$ (from the complex impedance sensor 64 or the memory 80, for example) corresponding to a point in time subsequent to time $t_1$ (i.e., time $t_2$), the ECU 34 is configured to calculate the slope (m) of the line between these two reactance values using equation (6):

$$m = \frac{X_2 - X_1}{t_2 - t_1} \quad (6)$$

wherein $X_2$ and $X_1$ are reactance values, and $t_2$ and $t_1$ are times to which the reactance values correspond. Accordingly, the ECU 34 is configured to calculate the change in reactance and the change in time, and to then divide the change in reactance by the change in time to solve for the slope, and therefore, the index. Once the index is calculated, the ECU 34 may display the index for the user to see, and/or evaluate the index to determine whether there is a risk or likelihood of barotrauma occurring in the tissue 12 (Step 134). More particularly, in an exemplary embodiment, the ECU 34 determines whether the slope value is a positive or a negative value. In an exemplary embodiment, if the value is positive, then the ECU 34 can determine that there has not been a decrease in the reactance, and therefore, there is currently no risk or likelihood of barotrauma occurring in the tissue 12. In such an instance, the ECU 34 and may or may not provide the user of the system 10 with an indication of this determination. The ECU 34 may then repeat the process for the next reactance value sample corresponding to a subsequent point in time (i.e., time $t_3$), and so on and so forth. If, however, the slope value is negative, the ECU 34 can determine that the reactance has decreased, and therefore, there is a risk or likelihood of barotrauma occurring in the tissue 12. The ECU 34 may then, as is described elsewhere herein, provide the user with an alert or some other indicator to advise the user of the likelihood of barotrauma occurring in the tissue 12 so that the user may take corrective or preventive action. Additionally, or in the alternative, the ECU 34 may cause the value of the index to be displayed for the user to see and interpret.

With reference to FIG. 10, in another exemplary embodiment, rather than calculating the slope based on the reactance value at the commencement of the lesion formation process and the reactance value a time subsequent thereto, the ECU 34 is configured to calculate the slope, and therefore the index, based on a current reactance value (e.g., $X_2$) (i.e., a reactance value between the electrode 16 and the tissue 12 at the time of the calculation, or a previous reactance value sampled more recently than the other reactance value (e.g., $X_1$) being taken into account) and a prior reactance value (e.g., $X_1$) sampled at a point in time after the start of the lesion formation process but before the sampling of the current reactance value (e.g., $X_2$) (accordingly, the prior reactance value may be the reactance value at the commencement of the lesion formation process, or may be a value corresponding to point in time subsequent thereto). In such an embodiment, and as described above, the ECU 34 is configured to sample the value of the reactance between the electrode 16 and the tissue 12 at a predetermined rate, and to store each sampled value in a memory or storage device described elsewhere herein along with its corresponding time. As with the embodiment described above and illustrated in FIG. 9, the ECU 34 may calculate the slope for each reactance value sampled, or may calculate the change in reactance after a certain number of reactance value samples have been collected or after a certain amount of time has elapsed. For ease of description purposes, however, the description below will be limited to an embodiment wherein the slope is calculated after each reactance value sample is collected. It will be appreciated in view of the above, however, that the present disclosure is not limited to such an embodiment.

Accordingly, with continued reference to FIG. 10, the ECU 34 is configured to acquire a current reactance value $X_2$ (Step 130') (from the complex impedance sensor 64 or from the memory 80, for example). The ECU 34 is configured to then acquire (from the memory 80, for example) a reactance value $X_1$ sampled prior to the time at which the reactance value $X_2$ was sampled (Step 128'). The prior reactance value $X_1$ may be the most immediate prior reactance value to the current reactance value $X_2$, or may be another prior reactance value chosen based on certain criteria (e.g., a value acquired a certain amount of time prior to the current time, a value acquired a certain number of collected samples prior, etc.). In any event, once the ECU 34 has acquired the current and prior reactance values, it is configured to calculate the slope, and therefore, the index, using equation (6) above (Step 132), and to evaluate/process the index (Step 134), in the same manner described above with respect to FIG. 9. Accordingly, the description of the calculation and processing of the index will not be repeated here.

Whether the index is calculated based on the change in impedance or the slope of the line between two reactance values, in an exemplary embodiment, rather than determining the likelihood of barotrauma based solely on whether the index is positive or negative, the ECU 34 is further configured to compare the negative value to a predetermined threshold, and to then determine whether there is a likelihood of barotrauma occurring in the tissue 12.

In such an embodiment, the system 10, and the ECU 34, in particular, is programmed with, or configured to access, an index threshold value corresponding to a barotrauma threshold. In one embodiment, the threshold may be the minimum index value at which it is likely that barotrauma will occur. Alternatively, the threshold may be the maximum index value at which it is not likely that barotrauma will occur. In either instance, the threshold value is determined by experimentation and/or analysis performed prior to the use of the system 10 (i.e., as part of the manufacturing or set up process, for example), and may be impacted by factors such as, for example, the type of catheter used, the type of ablation generator, and other characteristics relating to, for example, the equipment of the system 10. In such an embodiment, the index value is compared to the threshold value (Step 138) and, based on the comparison, an indication may be provided to the user that there is an increased chance or likelihood of barotrauma occurring in the tissue 12 (Step 136) (e.g., if the index meets or exceeds the threshold). An indication may also be provided to the user that barotrauma is not likely to be caused in the tissue 12 (e.g., if the index falls below the threshold value).

In an exemplary embodiment, the threshold value is set prior to the system 10 being used and is not adjustable. Alternatively, in an other exemplary embodiment, the threshold may be adjustable by the user to change the sensitivity of the system 10. In the latter embodiment, the system 10 may include a user interface, such as, for example, the user input device 82 described above (e.g., a touch screen, a keyboard, a keypad, a slider control, or some other user-controllable input device that is electrically connected to the ECU 34), to allow the user to adjust the threshold value, and therefore, the sensitivity of the system 10.

In another exemplary embodiment, rather than comparing the index to a threshold value, as was described in greater detail above, the index may be displayed (Step 136) for the user to see and react to, if necessary; or may be used in conjunction with a look-up table stored on, or accessible by, the ECU 34 to determine whether the index value is such that a warning should be provided to the user.

As briefly described above, irrespective of how the index is calculated (i.e., the change in reactance or the slope of a line between two reactance values), and whether or not it is compared to a threshold value, in an exemplary embodiment, the system 10 may be configured to cause an appropriate indicator to be given to the user of the system 10 in response to the index calculation. In one embodiment, the ECU 34 is configured to generate a signal representative of an indicator corresponding to the index value and/or the likelihood of a barotrauma occurring in the tissue 12. The indicator may take many forms. For example, the indicator may be displayed on the display monitor 36. Such a displayed indicator may include, for exemplary purposes only, displaying the calculated index value or an alert or warning message on the monitor 36. In other exemplary embodiments, the indicator may take the form of an audible alert, a visible indication on the catheter handle or another device of the system 10, haptic feedback, a binary type output (e.g., "light on"/"light off"), a gas gauge type of output, or any other indicators known in the art. Based on the indicator provided to the user, the user may take corrective measures, such as, for example and without limitation, moving the electrode 16 away from the tissue, reducing the RF power being applied to tissue, and/or other the like measures.

As described above, once the index has been calculated for value(s) sampled at a predetermined point in time, the process repeats itself for subsequent value(s) sampled at a subsequent point in time in accordance with a predetermined rate of calculating the index (e.g., for each value or set of values sampled; after a certain number of samples are collected; after predetermined amount of time has elapsed, etc.). The process may be continuously repeated at a given rate until the lesion has been formed, or the formation process has been otherwise stopped.

As briefly described above, in an exemplary embodiment, the ECU 34 is further configured to assess the stability of the position of the catheter 18, and therefore the electrodes 16, 52, 54 thereof, and to take the stability into consideration in determining the likelihood of barotrauma occurring in the tissue 12. One reason that it may be desirable to assess the stability of the catheter 18 and the electrodes associated therewith is that while changes in the values of the components of the complex impedance between the electrode 16 and the tissue 12 can occur when the catheter 18 is stable, similar changes may occur if the catheter 18 moves (i.e., its position is unstable). Consequently, if the stability of the catheter 18 and the electrodes 16, 52, 54 is not taken into consideration, false predictions of barotrauma occurrence may result.

The stability of the catheter 18 and the associated electrodes may be assessed at any number of points in time, and any number of times. For example, the stability may be assessed prior to the ECU 34 acquiring values for one or more components of the complex impedance, after the acquisition of the value(s) of the complex impedance component(s) but before the calculation of the index, and/or after the calculation of the index but prior to the processing of the index or the provision of an indicator relating thereto. However, for purposes clarity and illustration only, the description below will be limited to an embodiment wherein the stability is assessed prior to acquiring value(s) of one or more components of the complex impedance between the electrode 16 and the tissue 12.

Figure 11:
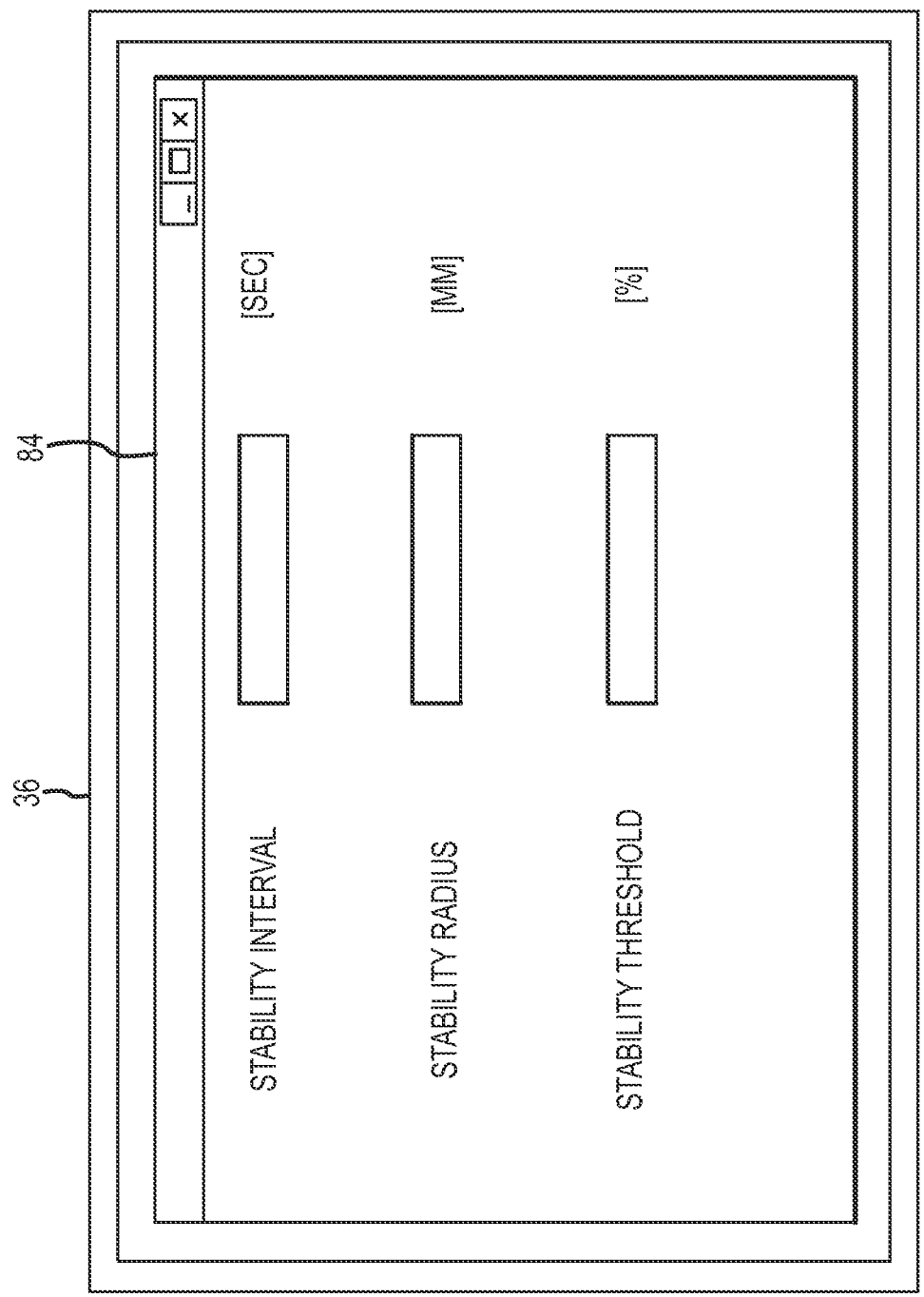
FIG. 11 is an exemplary embodiment of a display device of the system illustrated in FIG. 1 with a graphical user interface (GUI) displayed thereon.

The stability may be determined in any number of ways, such as, for example, as described in U.S. patent application Ser. No. 12/964,910 filed Dec. 10, 2010, and entitled "System and Method for Presenting Information Representative of Lesion Formation in Tissue During an Ablation Procedure" (docket no. 0G-045700US), the entire disclosure of which is hereby incorporated by reference. In one exemplary embodiment, the ECU 34 is configured to assess the displacement of the catheter 18, and therefore, one or more electrodes thereof (e.g., one or more positioning electrodes, such as, for example, positioning electrode 52), over a predetermined stability time interval. The ECU 34 may be pre-programmed with a stability time interval, or the interval may be defined by the user or clinician using an input device, such as, for example, a graphical user interface (GUI) 84 having one or more user-inputable or user-selectable input fields, an exemplary embodiment of which is illustrated in FIG. 11, or the user input device 82 described above and illustrated, for example, in FIG. 1. Accordingly, the ECU 34 is configured to sample the position of the catheter 18 using the techniques described in greater detail above, for example, at a predetermined rate over the stability time interval, and to then calculate a displacement between each sampled position and one or more positions previously acquired during the stability time interval.

Figure 12A:
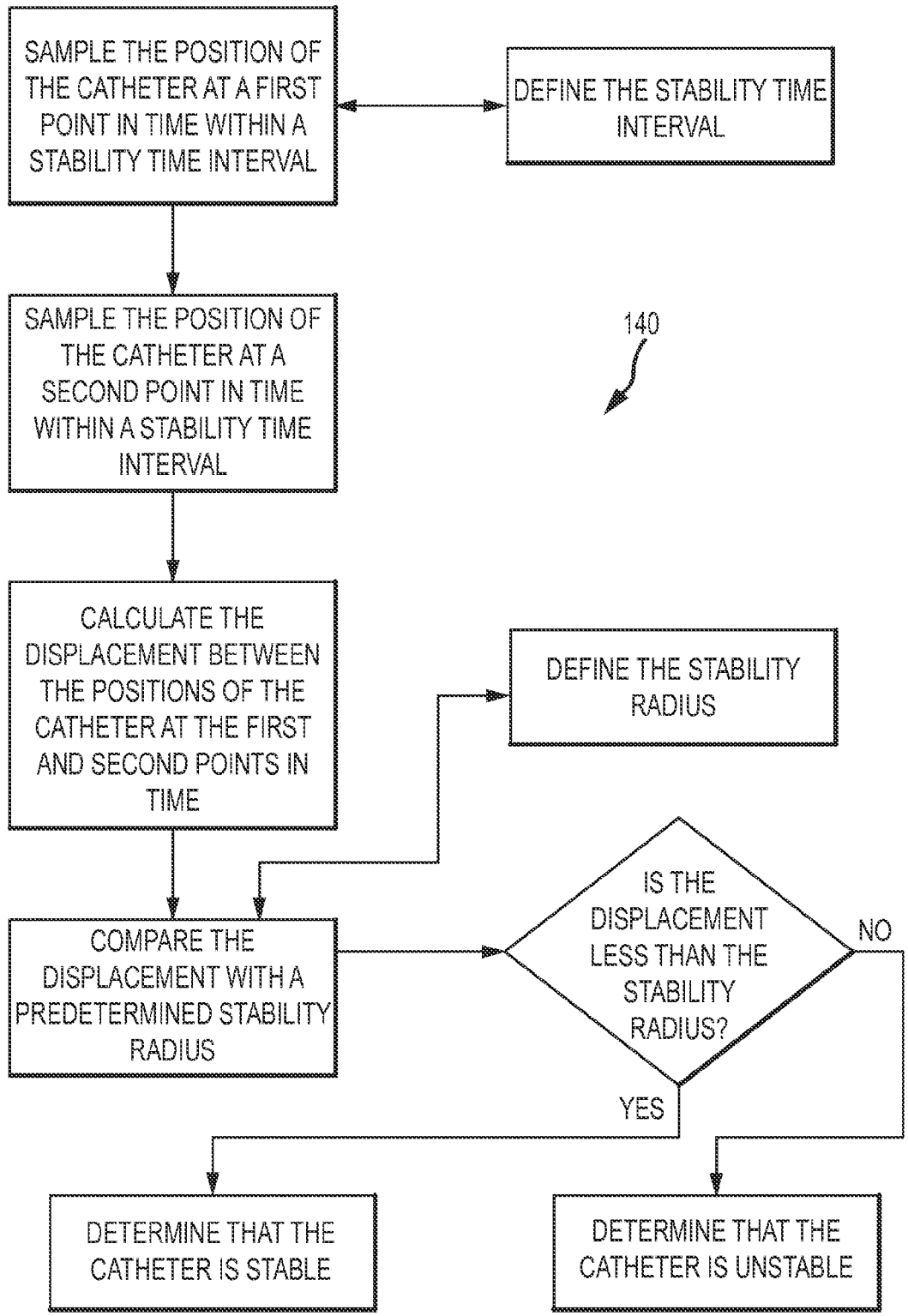
FIGS. 12a-12c are flow charts illustrative of exemplary embodiments of methodologies for assessing the stability of a positioning electrode, and therefore, catheter associated therewith.

For example and as illustrated in FIG. 12a, the ECU 34 acquires a first position of the positioning electrode 52 at a first time during the stability time interval and stores the position in, for example, a memory or storage medium that is part of or accessible by the ECU 34 (e.g., the memory 80). The ECU 34 acquires a second position of the electrode 52 at a second point in time during the defined stability time interval, and then calculates the displacement between the two positions. The ECU 34 then acquires a third position of the electrode 52 at a third point in time in the stability time interval, and then calculates the displacement between it and the first position.

In an exemplary embodiment, the ECU 34 is further configured to compare each calculated displacement with a predetermined stability radius and to determine, based on the comparison, whether the catheter 18, and therefore, the electrodes thereof, is stable. More specifically, if the displacement meets or is less than the stability radius, a determination can be made that the catheter 18 is stable. If, however, the displacement is above the stability radius, a determination can be made that the catheter 18 is not stable. As with the stability time interval, the ECU 34 may be pre-programmed with a stability radius, or the radius may be defined by the user or clinician using an input device, such as, for example, the GUI 84 illustrated in FIG. 11. This stability assessment may be performed for each acquired position, or at some other predetermined rate, such as, for example, after a certain amount of time has elapsed, or after a certain number of positions have been acquired (e.g., stability is assessed every fifth sample, for example).

Figure 12B:
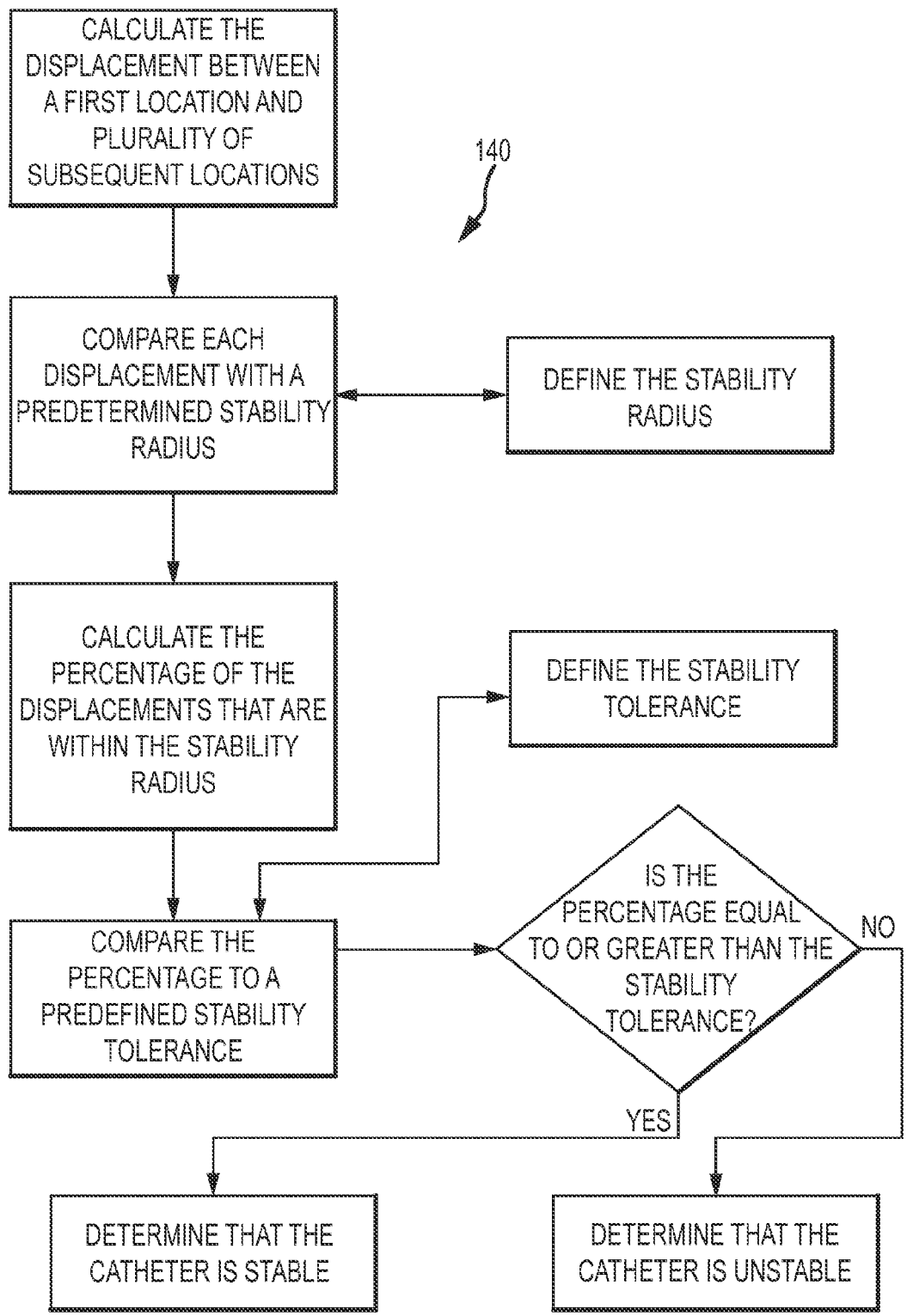

In an exemplary embodiment, in addition to the stability time interval and the stability radius, the stability may be assessed using the additional criteria of a stability tolerance. The stability tolerance represents the percentage of displacements that must be within the stability radius for the catheter to be deemed stable. Accordingly, if the stability tolerance is 90%, then 90% of the displacements over the stability interval must be within the stability radius for the catheter to be deemed stable. As with both the stability time interval and the stability radius, the ECU 34 may be pre-programmed with a stability tolerance, or the tolerance may be defined by the user or clinician using an input device, such as, for example, the GUI 84 illustrated in FIG. 11. Accordingly, in an exemplary embodiment illustrated, for example, in FIG. 12b, a series of displacements are calculated over the stability interval and some or all of them are compared with the stability radius. The ECU 34 then determines what percentage of the calculated displacements were within the stability radius, and compares that percentage to the stability tolerance. If the percentage meets or exceeds the tolerance, then the catheter may be deemed to be stable. On the other hand, if the percentage is less than the tolerance, then the catheter may be deemed to be unstable.

Figure 12C:
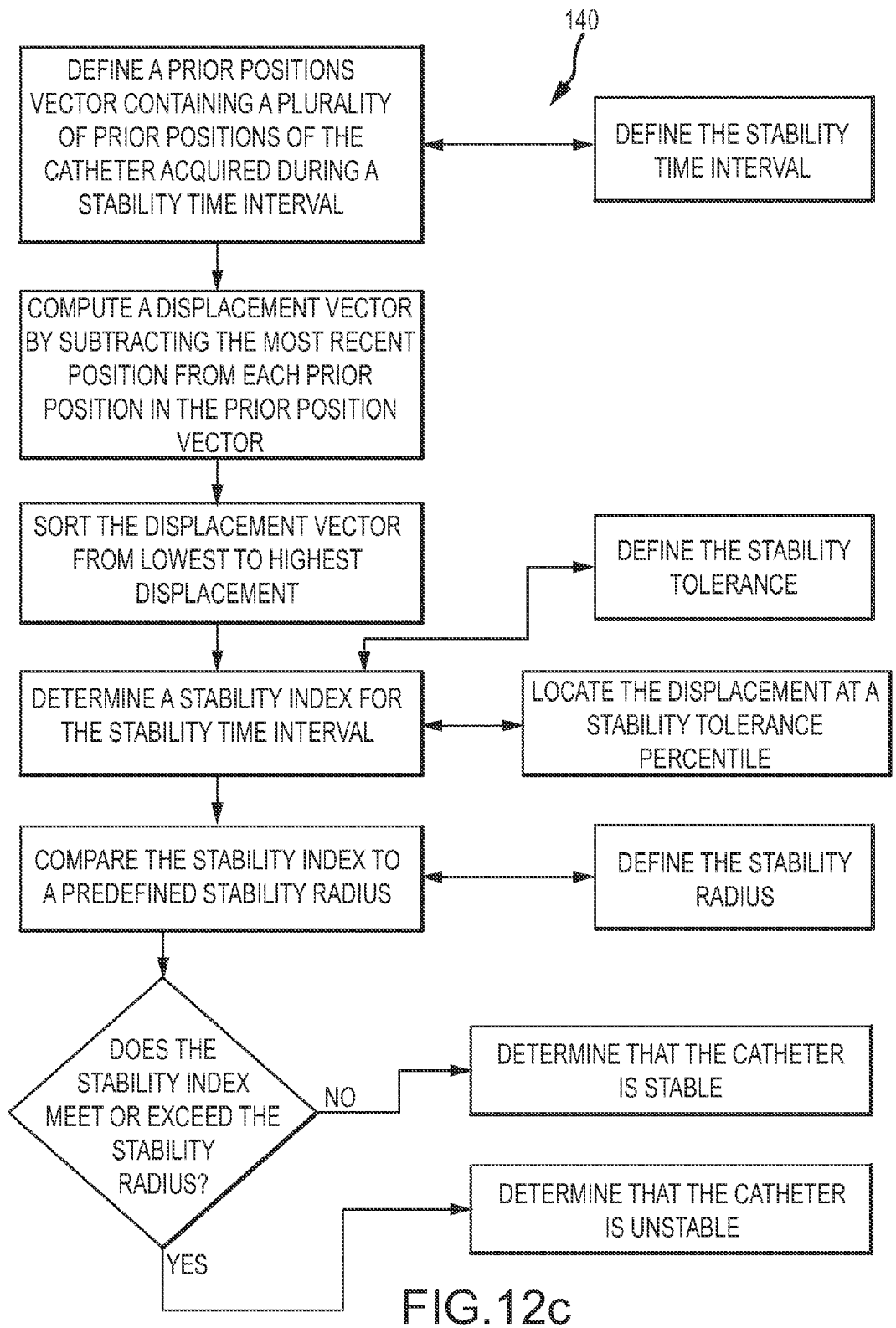

In another exemplary embodiment illustrated, for example, in FIG. 12c, the ECU 34 is configured to assess the stability of the catheter 18 by computing a stability index. The ECU 34 may take into account the stability time interval, the stability radius, and the stability tolerance in this assessment, and the assessment may be a real time running assessment.

More particularly, in an exemplary embodiment, the ECU 34 is configured to define a prior positions vector that contains some or all of the positions that are acquired by the ECU 34 within the most recent stability time interval (i.e., if the stability time interval is 20 seconds (20 s), all of the positions acquired within the past 20 s). The ECU 34 is also configured to compute a displacement vector by subtracting the most recent position from each position in the previous positions vector. Once the displacement vector is computed, the ECU 34 is configured to sort the displacement vector. In an exemplary embodiment, the displacement vector is sorted from the lowest displacement to the highest displacement. Using the sorted displacement vector, the ECU 34 is configured to then determine the stability index for the stability time interval. In one exemplary embodiment, the stability index is defined as the displacement at the stability tolerance percentile. Accordingly, the ECU 34 is configured to identify the displacement in the displacement vector that corresponds to the stability tolerance, and to then define the stability index to be the corresponding displacement. For example, if there are ten (10) displacements in the displacement vector and the stability tolerance is 90%, the ECU 34 would locate the ninth displacement in the sorted displacement vector by starting at the lowest displacement in the vector and counting upwards in the vector until the ninth displacement is reached. If the displacement at the ninth position in the sorted displacement vector is 3 mm, then the ECU 34 defines the stability index to be 3 mm. Once the stability index is defined, in an exemplary embodiment, the stability is assessed by comparing the stability index to the stability radius in the same manner described above. Accordingly, if the stability index exceeds (or in some instances meets or exceeds) the stability radius, the ECU 34 may determine that the catheter 18 is not stable. Alternatively, if the stability index falls below (or in some instances meets or falls below) the stability radius, the ECU 34 may determine that the catheter is stable.

In an exemplary embodiment, the ECU 34 may also compensate for motion occurring within the region in which the catheter 18 is disposed in the stability assessment. As described above, motion may be caused by, for example, cyclic body activities, such as, for example, cardiac and/or respiratory activity. Accordingly, the ECU 34 may incorporate, for example, cardiac and/or respiratory phase into the stability assessment.

For example, in one embodiment, the ECU 34 may be further configured to employ time-dependent gating in an effort to increase accuracy of the stability assessment. In general terms, time-dependent gating comprises monitoring a cyclic body activity and generating a timing signal, such as an organ timing signal, based on the monitored cyclic body activity. The organ timing signal may be used for phase-based stability assessment, thereby resulting in more accurate stability assessment throughout an ablation procedure and the different phases of the cyclic activity.

For the purposes of clarity and brevity, the following description will be limited to the monitoring of the cardiac cycle. It will be appreciated, however, that other cyclic activities (e.g., respiratory activity, combination of cardiac and respiratory activities, etc.) may be monitored in similar ways and therefore remain within the spirit and scope of the present invention. Accordingly, in an exemplary embodiment, the system 10 includes a mechanism to measure or otherwise determine a timing signal of a region of interest of the patient's body, which, in an exemplary embodiment, is the patient's heart, but which may also include any other organ that is being evaluated. The mechanism may take a number of forms that are generally known in the art, such as, for example, a conventional electro-cardiogram (ECG) monitor. A detailed description of a ECG monitor and its use/function can be found with reference to U.S. Patent Publication No. 2010/0168550 entitled "Multiple Shell Construction to Emulate Chamber Contraction with a Mapping System," which is incorporated herein by reference in its entirety.

In general terms, an ECG monitor is provided that is configured to continuously detect an electrical timing signal of the patient's heart through the use of a plurality of ECG electrodes, which may be externally-affixed to the outside of a patient's body. The timing signal generally corresponds to the particular phase of the cardiac cycle, among other things. In another exemplary embodiment, rather than using an ECG to determine the timing signal, a reference electrode or sensor positioned in a fixed location in the heart may be used to provide a relatively stable signal indicative of the phase of the heart in the cardiac cycle (e.g., placed in the coronary sinus). In still another exemplary embodiment, a medical device, such as, for example, a catheter having an electrode may be placed and maintained in a constant position relative to the heart to obtain a relatively stable signal indicative of cardiac phase. Accordingly, one of ordinary skill in the art will appreciate that any number of known or hereinafter developed mechanisms or techniques, including but not limited to those described above, may be used to determine a timing signal.

Once the timing signal, and therefore, the phase of the patient's heart, is determined, the position information corresponding to the position of the positioning electrode 52 may be segregated or grouped into a plurality of sets based on the respective phase of the cardiac cycle during (or at which) each position was collected. Once the position information is grouped, the ECU 34 is configured to determine the stability of the catheter 18 for one or more phases of the cardiac cycle in the manner described above using only those positions of the positioning electrode 52 that were collected during that particular phase for which the stability is being assessed. Because the timing signal is known, as each subsequent position of the positioning electrode 52 is acquired, the position is tagged with a respective time-point in the timing signal and grouped with the appropriate previously recorded position information. The subsequent positions may then be used to assess the stability of the catheter 18 for the phase of the cardiac cycle during which the position was collected. If desired, the overall stability over multiple phases of the cyclic activity may also be determined. For example, if the catheter 18 is determined to be unstable during any one phase of the cyclic activity, the ECU 34 may deem the catheter 18 to be unstable. In another exemplary embodiment wherein the stability is assessed using the stability index described above, the smallest stability index of any of the phases may be compared to the stability radius to determine stability. Accordingly, stability may be assessed on a phase-by-phase basis, or on a combination of phases basis.

In another exemplary embodiment, in addition to assessing stability using the criteria and techniques described above, the ECU 34 is configured to assess the stability of the catheter 18 by taking into account the length of time that the stability criteria are met. More particularly, the ECU 34 may be configured to determine the whether stability criteria is met using the techniques described above, to calculate the length of time that the catheter 18 is continuously deemed to be stable, to compare the calculated length of time with a predetermined time value (i.e., stability hold), and to determine, based on the comparison, where the catheter can be said to be stable. If the catheter 18 is stable for a period of time that meets or exceeds the stability hold time value, the ECU 34 may determine that the catheter is stable. If, on the other hand, the catheter is stable for a time less than the stability hold time value, but then becomes unstable prior to the threshold being met, the ECU 34 may determine that the catheter is unstable, and as a result, the stability time resets. The ECU 34 may be preprogrammed with the time value, or the time value may be defined by the user or clinician using an input device, such as, for example, the GUI 84.

As briefly described above, once the stability of the catheter 18, therefore, the electrodes 16, 52, 54 thereof has been assessed or determined, it may be taken into consideration in determining the likelihood of barotrauma occurring in the tissue 12.

More particularly, the ECU 34 may be configured to take certain action only if the catheter 18 is determined to be stable (i.e., meets certain stability criteria). For example, the ECU 34 may be configured to acquire one or more values of one or more components of the complex impedance between the tissue 12 and the electrode 16 only if the catheter 18/electrode 16 is stable. Similarly, the ECU 34 may be configured to calculate the index, process the calculated index, and/or provide an indicator based on the calculated index only if the catheter 18/electrode 16 is stable. Conversely, if the ECU 34 determines that the catheter 18/electrode 16 does not meet certain stability criteria, and therefore, is unstable, the ECU 34 will not perform one or more of the actions described above. In an exemplary embodiment, the ECU 34 may be further configured to provide the user an indication of the stability.

In accordance with another aspect of the disclosure, the system 10 may take the form of an automated catheter system 86, such as, for example and without limitation, a robotic catheter system or a magnetic-based catheter system. As will be described below, the automated catheter system 86 may be fully or partially automated, and so may allow for at least a measure of user control through a user input.

In the embodiment wherein the automated catheter system 86 is a robotic catheter system (i.e., robotic catheter system 86), a robot is used, for example, to control the movement of the catheter 18 and/or to carry out therapeutic, diagnostic, or other activities. In an exemplary embodiment, the robotic catheter system 86 may be configured such that information relating to the calculated index likelihood of barotrauma occurrence in the tissue 12 may be communicated from the ECU 34 to a controller or control system 88 of the robotic catheter system 86. In an exemplary embodiment, the ECU 34 and the controller 88 are one in the same. However, in another exemplary embodiment, the two are separate and distinct components. For ease of description purposes only, the following description will be directed to the latter, separate and distinct arrangement. It should be noted, however, that the embodiment wherein the controller 88 and the ECU 34 are the same remains within the spirit and scope of the present disclosure.

Figure 13:
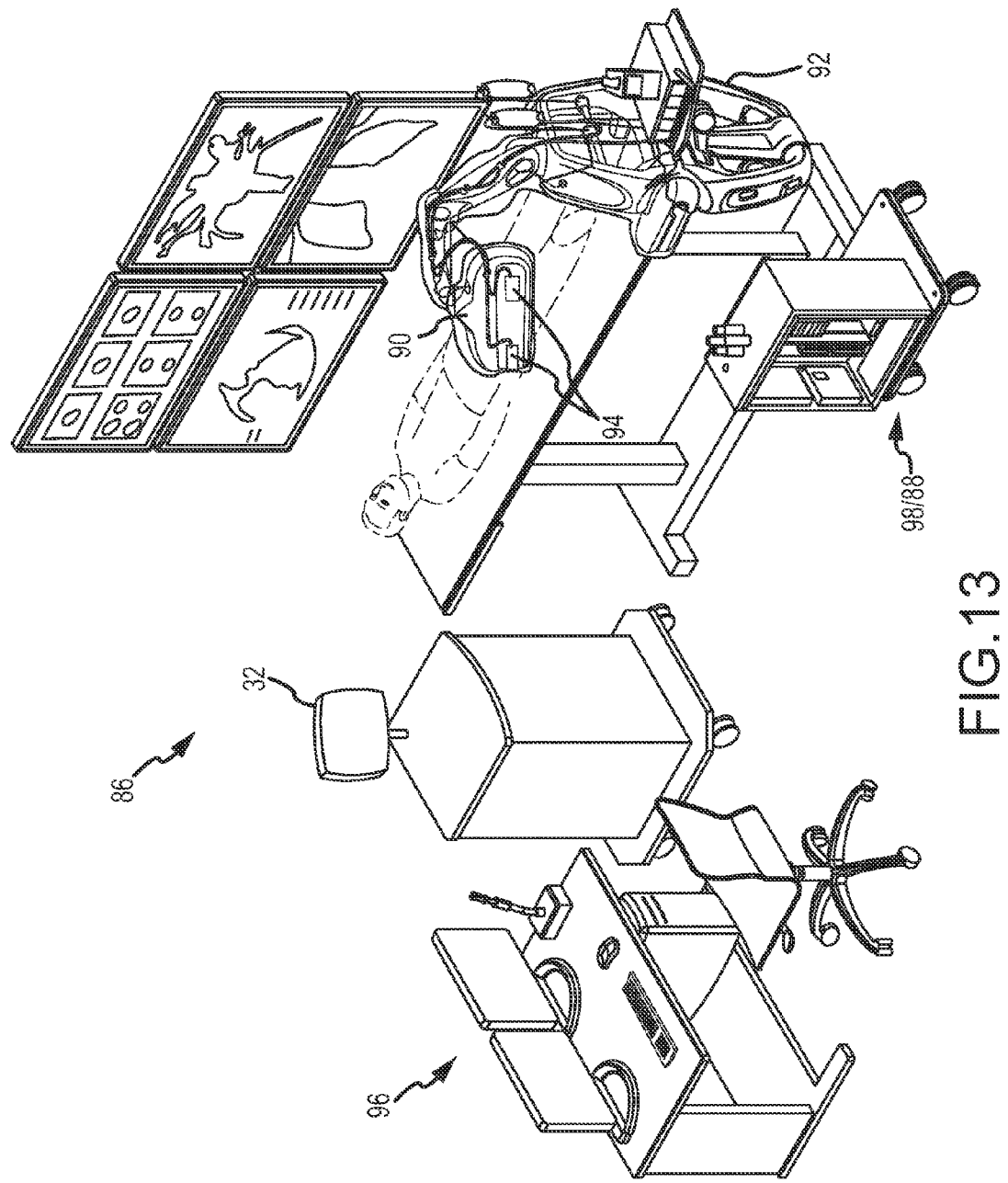
FIG. 13 is an isometric diagrammatic view of a robotic catheter system illustrating an exemplary layout of various system components in accordance with the present teachings.
Figure 14:
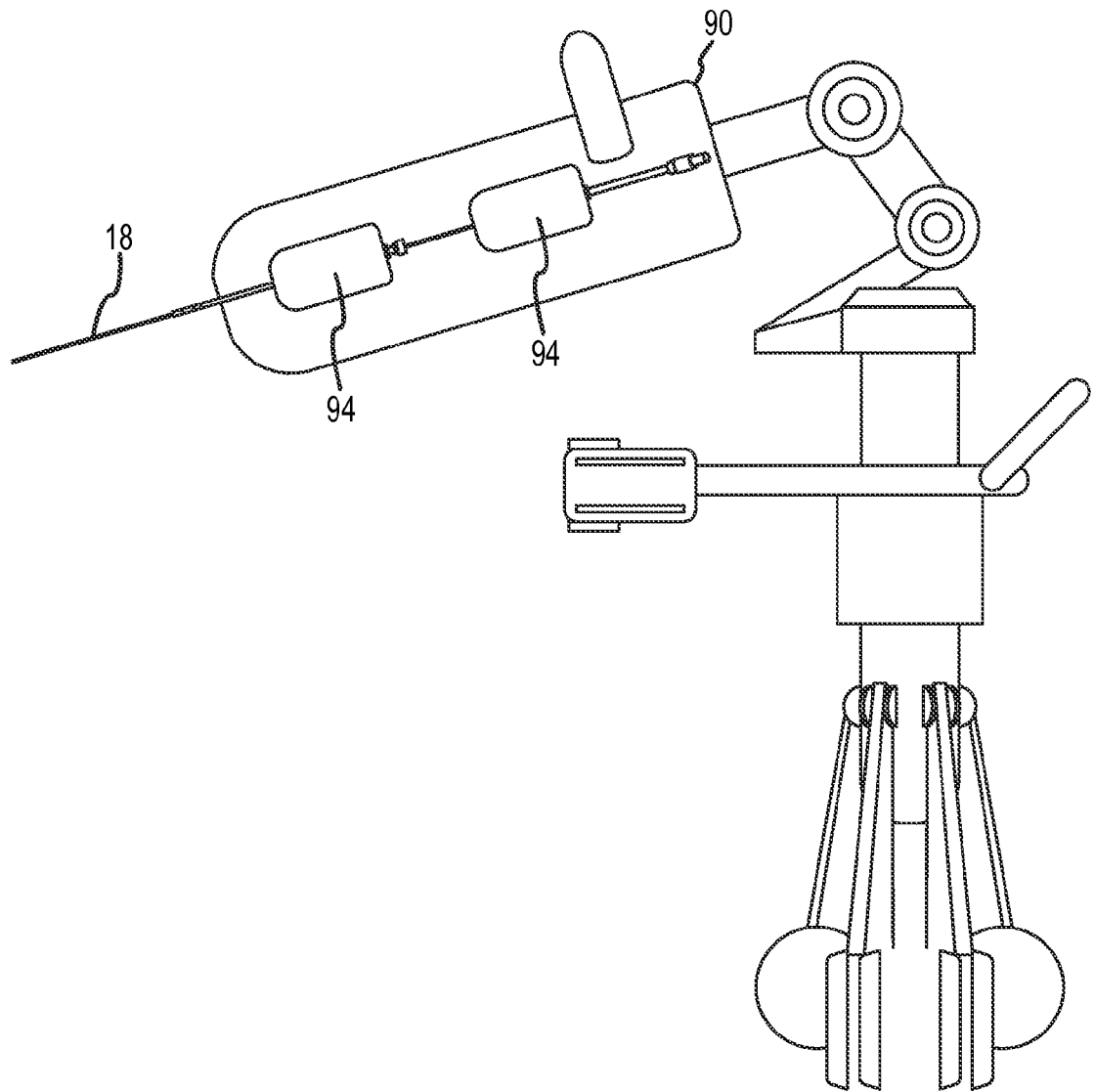
FIG. 14 is an isometric diagrammatic view of an exemplary embodiment of a robotic catheter manipulator support structure in accordance with the present teachings.

The information communicated to the controller 88 may be in the form of the signal(s) described above representative of an indicator relating to the index value or the likelihood of barotrauma occurrence. As will be described in greater detail below, the controller/control system 88 may use this information in the control and operation of the robotic catheter system 86. With reference to FIGS. 13 and 14, the robotic catheter system 86 will be briefly described. A full description of the robotic catheter system 86 is set forth in commonly-assigned and co-pending U.S. patent application Ser. No. 12/347,811 entitled "Robotic Catheter System," the disclosure of which is hereby incorporated by reference herein in its entirety.

Accordingly, FIGS. 13 and 14 illustrate the robotic catheter system 86. The robotic catheter system 86 provides the ability for precise and dynamic automated control in, for example, diagnostic, therapeutic, mapping, and ablative procedures. In an exemplary embodiment, the robotic catheter system 86 includes one or more robotic catheter manipulator assemblies 90 supported on a manipulator support structure 92. The robotic catheter manipulator assembly 90 may include one or more removably mounted robotic catheter device cartridges 94, for example, that are generally linearly movable relative to the robotic catheter manipulator assembly 90 to cause the catheter associated therewith (i.e., catheter 18) to be moved (e.g., advanced, retracted, etc.). The catheter manipulator assembly 90 serves as the mechanical control for the movements or actions of the cartridge 94. The robotic catheter system 86 may further include a human input device and control system ("input control system") 96, which may include a joystick and related controls with which a physician/clinician may interact to control the manipulation of the cartridge 94, and therefore, the catheter 18 of the system 86. The robotic catheter system 86 may still further include an electronic control system 98, which, in an exemplary embodiment, consists of or includes the controller 88, which translates motions of the physician/clinician at the input device into a resulting movement of the catheter. As with the system 10 described above, the robotic catheter system 86 may further include the visualization, mapping and/or navigation system 32, to provide the clinician/physician with real-time or near-real-time positioning information concerning the catheter and various types of anatomical maps, models, and/or geometries of the cardiac structure of interest, for example.

In addition to, or instead of, the manual control provided by the input control system 96, the robotic catheter system 86 may involve automated catheter movement. For example, in one exemplary embodiment, a physician/clinician may identify locations (potentially forming a path) on a rendered computer model of the cardiac structure. The system 86 can be configured to relate those digitally selected points to positions within the patient's actual/physical anatomy, and may command and control the movement of the catheter 18 to defined positions. Once in a defined position, either the physician/clinician or the system 86 could perform desired treatment or therapy, or perform diagnostic evaluations. The system 86 could enable full robotic control by using optimized path planning routines together with the visualization, mapping, and/or navigation system 32.

As briefly described above, in an exemplary embodiment, information relating to the calculated index and/or a determination as to the likelihood of barotrauma occurring in the tissue 12 is input into controller 88 and may be used in the control and operation of the robotic catheter system 86. In an exemplary embodiment, the information (i.e., index, determination of likelihood of barotrauma) is generated by, for example, the ECU 34 as described in great detail above. This information is then communicated by the ECU 34 to the controller 88. In one exemplary embodiment the information is simply stored within the robotic catheter system 86. Accordingly, no affirmative action is taken by the controller 88, or any other component of the robotic catheter system 86, in response to the information. In another exemplary embodiment, however, the information may be used by the robotic catheter system 86 to control one or more aspects of the operation of the system 86.

More particularly, in an exemplary embodiment, when it is determined, based on the calculated index described in great detail above, that it is likely a barotrauma will occur in the tissue 12, the controller 88 may be configured to retract or move the catheter 18 away from the tissue 12. The controller 88 may also be configured to cause the RF power being applied to the tissue 12 to be reduced or turned off completely. In such an instance, the controller 88 would be connected to the ablation generator 26 either directly or indirectly through, for example, the ECU 34 to allow communication between the controller 88 and the ablation generator 26 to reduce or turn-off the power applied to the tissue 12.

In another exemplary embodiment, instead of the controller 88 taking the affirmative steps to move away from the tissue or causing the power applied to the tissue 12 to be reduced or turned off, the controller 88 is configured to inquire as to whether the ablation procedure should go on, whether the controller 88 should move the catheter 18, whether the power should be reduced, etc. This inquiry may be directed to a physician/clinician, the ECU 34, or another component within the system 86. Depending on the feedback the controller 88 receives, it may take the necessary actions to carry out the instructions embodied by the feedback.

Figure 15:
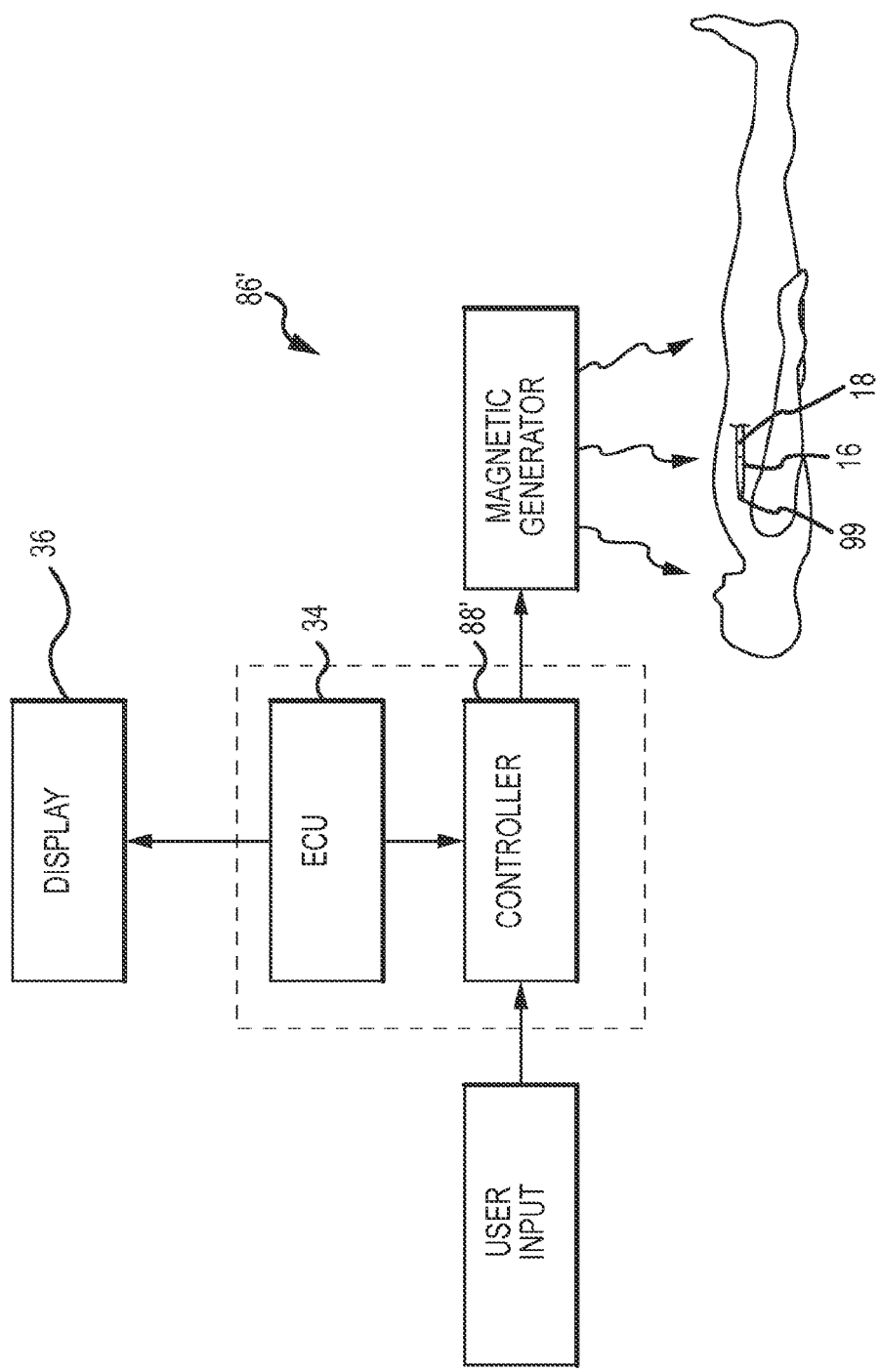
FIG. 15 is a schematic diagram of a magnetic-based catheter manipulation system in accordance with the present teachings.

With reference to FIG. 15, an exemplary embodiment of the automated catheter guidance system 86 comprising a magnetic-based catheter system (i.e., magnetic-based catheter system 86') is illustrated. In one exemplary embodiment, one or more externally generated magnetic fields produced by one or more electromagnets are used to move, guide, and/or steer a magnetically-tipped catheter through a patient's body. The externally generated magnetic fields exert a desired torque on the catheter to cause the position of the catheter to be manipulated in a desired way (e.g., advance, retract, bend, rotate, speed up, slow down, etc.). Accordingly, as with the robotic catheter system described above, the magnetic fields may be used to control the movement of the catheter 18 and/or to allow the system 10 to carry out therapeutic, diagnostic, or other activities at given locations within the patient's body. A full description of a magnetic-based catheter system is set forth in U.S. Pat. No. 6,507,751 entitled "Method and Apparatus Using Shaped Field of Repositionable Magnet to Guide Implant," and U.S. Published Patent Application No. 2007/0016006 A1 entitled "Apparatus and Method for Shaped Magnetic Field Control for Catheter, Guidance, Control, and Imaging," the disclosures of which are hereby incorporated by reference herein in their entireties.

In an exemplary embodiment, the magnetic-based catheter system 86' may be configured such that information relating to the calculated index or the determination as to the likelihood of barotrauma occurrence in the tissue 12 may be communicated from the ECU 34 to a controller or control system 88' of the magnetic-based catheter system 86'. In an exemplary embodiment, the ECU 34 and the controller 88' are one in the same. However, in another exemplary embodiment, the two are separate and distinct components. For ease of description purposes only, the following description will be directed to the latter, separate and distinct arrangement. It should be noted, however, that the embodiment wherein the controller 88' and the ECU 34 are the same remains within the spirit and scope of the present disclosure.

The information communicated to the controller 88' may be in the form of the signal(s) described above representative of the calculated index or the determination of the likelihood of barotrauma occurring in the tissue 12. As will be described in greater detail below, the controller/control system 88' may use this information in the control and operation of the magnetic-based catheter system 86'.

As with the robotic catheter system described above, the magnetic-based catheter system 86' provides the ability for precise and dynamic automated control in, for example, diagnostic, therapeutic, mapping, and ablative procedures. In an exemplary embodiment, the magnetic-based catheter system 86' includes somewhat similar structure to that of the robotic catheter system described above to effect the movement of the catheter 18. For example, system 86' may comprise a catheter manipulator assembly that includes, in part, one or more external magnetic field generators configured to create the magnetic field(s) required to induce the movement of the catheter 18, and a magnetic element 99 mounted thereon or therein. The system 86' may further comprise support structures and the like to support catheter 18. As also with the robotic catheter system, the magnetic-based catheter system 86' may further include a human input device and control system ("input control system"), which may include a joystick and related controls with which a physician/clinician may interact to control the manipulation the catheter 18. In one exemplary embodiment, the system 86' is configured such that the physician or clinician may input a command for the catheter to move in a particular way. The system 86' processes that input and adjusts the strength and/or orientation of the external magnetic fields to cause the catheter 18 to move as commanded. The magnetic-based catheter system 86' may also still further include an electronic control system, which, as with the electronic control system of the robotic catheter system described above, may consist of or include the controller 88', that translates motions of the physician/clinician at the input device into a resulting movement of the catheter. Finally, in an exemplary embodiment, the magnetic-based catheter system 86' may further include the visualization, mapping and navigation system 32, to provide the clinician/physician with real-time or near-real-time positioning information concerning the catheter and various types of anatomical maps, models, and/or geometries of the cardiac structure of interest, for example.

As briefly described above, in an exemplary embodiment, information relating to the calculated index and/or the determination as to the likelihood of barotrauma occurring in the tissue 12 is input into controller 88' and may be used in the control and operation of the magnetic-based catheter system 86'. In an exemplary embodiment, the information is generated by, for example, the ECU 34 as described in great detail above. This information is then communicated by the ECU 34 to the controller 88'. In one exemplary embodiment the information is simply stored within the magnetic-based catheter system 86'. Accordingly, no affirmative action is taken by the controller 88', or any other component of the magnetic-based catheter system 86', in response to the information. In another exemplary embodiment, however, the information may be used by the magnetic-based catheter system 86' to control one or more aspects of the operation of the system 86'.

More particularly, in an exemplary embodiment, when it is determined, based on the calculated or determined index, that a barotrauma is likely to occur in the tissue 12, the controller 88' may be configured to retract or move the catheter 18 away from the tissue 12 by adjusting the strength and/or orientation of the external magnetic field. The controller 88' may also be configured to cause the RF power being applied to the tissue 12 to be reduced or turned off completely. In such an instance, the controller 88' would be connected to the ablation generator 26 either directly or indirectly through, for example, the ECU 34 to allow communication between the controller 88' and the ablation generator 26 to reduce or turn-off the power applied to the tissue 12.

In another exemplary embodiment, instead of the controller 88' taking the affirmative steps to move away from the tissue or causing the power applied to the tissue 12 to be reduced or turned off, the controller 88' is configured to inquire as to whether the ablation procedure should go on, whether the controller 88' should move the catheter 18, whether the power should be reduced, etc. This inquiry may be directed to a physician/clinician, the ECU 34, or another component within the system 86'. Depending on the feedback the controller 88' receives, it may take the necessary actions to carry out the instructions embodied by the feedback.

With reference to FIGS. 5-7 and 9-10, it will be appreciated that in addition to the structure of the system 10 and the article of manufacture described above, another aspect of the instant disclosure in accordance with present teachings is a method for determining a likelihood of barotrauma occurring in a tissue during the formation of a lesion in the tissue as a result of an ablation procedure being performed thereon is provided. It will be further appreciated that the methodology performed and carried out by the ECU 34 and described in great detail above applies to this aspect of the disclosure with equal force, and therefore, it will not be repeated in its entirety, rather a summary of the methodology will be provided.

With respect to FIG. 5, and in its most general form, one exemplary method includes a step 100 of acquiring, by, for example, the ECU 34, one or more values for one or more components of a complex impedance between the electrode 16 and the tissue 12. In an exemplary embodiment, a step 102 includes acquiring, by, for example, the ECU 34, a value for the power applied to the tissue 12 during the formation of the lesion therein. A step 104 includes calculating, by, for example, the ECU 34, an index responsive to the values for the one or more complex impedance components, and, in an exemplary embodiment, the applied power, wherein the index is indicative of a likelihood of barotrauma occurring in the tissue 12.

With reference to FIGS. 6 and 7, a more detailed description of exemplary embodiments of the method will be described. In these embodiments, values for first and second components of the complex impedance are acquired, and the first and second complex impedance components comprise resistance (R) and reactance (X). Accordingly, in substep 106 of the acquiring step 100, a value for the resistance between the electrode 16 and the tissue 12 is acquired by the ECU 34 corresponding to a point in time just before the commencement of a lesion formation process is to be performed on the tissue 12. In a substep 108 of the acquiring steps 100, 102, values for the resistance and reactance between the electrode 16 and the tissue 12, and a value of the power applied to the tissue corresponding to the time the lesion formation process commences, are acquired by the ECU 34. In a substep 110 of steps 100, 102, subsequent values for the resistance, reactance, and power at a point in time during the lesion formation process, and subsequent to the commencement of the lesion formation process, are acquired by the ECU 34 (i.e., in accordance with a predetermined sampling rate/predetermined time interval).

In a step 112, the ECU 34 calculates a change in resistance (dR) over the time interval between the start of the lesion formation process and the point in time at which the index is being calculated. In a step 114, the ECU 34 calculates or determines a change in time (dt) or the amount of elapsed time between the start of the lesion formation and the time at which the index is being calculated. In a step 120, the ECU 34 divides the change in resistance (dR) by the change in time (dt), the quotient of which is used by the ECU 34 in the index calculation.

In a step 116, the ECU 34 calculates a change in reactance (dX) over the time interval between the start of the lesion formation process and the point in time at which the index is being calculated. This change calculation is used by the ECU 34 in the index calculation.

In a step 118, an electrical current value is calculated by the ECU 34. This step includes a substep 122 of calculating a mean value for the power applied to the tissue 12 over the time interval between the start of the lesion formation process and the point in time at which the index is being calculated. The ECU 34 is configured to then divide the mean power value by the resistance value, $R_0$, corresponding to a point in time just before the lesion formation process commences; and to then take the square root of the quotient of the division operation to come to the electrical current value (I). The electrical current value (I) is used by the ECU 34 in the index calculation.

Once each of the above described calculations are made, the ECU 34 is configured to acquire the appropriate values for the constant and coefficients of the index equation, and to then process these values with the calculations described above to calculate the index (step 104). More particularly, the step 104 includes summing a predetermined constant with: the product of a first coefficient and the term (dR/dt); the product of a second coefficient and the electrical current value (I); the product of a third coefficient and the term dR, and the product of a fourth coefficient and the term dX.

With reference to FIG. 6, in an exemplary embodiment, the method further includes a step 124 that includes comparing, by, for example, the ECU 34, the calculated index to a predetermined index threshold to determine the likelihood of barotrauma occurring in the tissue 12. In an exemplary embodiment, if it is determined that there is an increased risk or chance of barotrauma occurring in the tissue 12, in a step 126 the ECU 34 is configured to generate a warning or alert signal or indicator, and control a display device, such as the display 36, to display the alert or warning represented by the signal generated by the ECU 34. If it is determined that barotrauma is not likely to occur, the ECU 34 may be configured to generate an indicator or signal corresponding this determination, and to control the display 36 to display such an indicator. The ECU 34 is further configured to repeat the above described methodology using R, X, and P samples corresponding to a subsequent point in time in the lesion formation process.

With reference to FIG. 7, in another exemplary embodiment, rather than comparing the calculated index to a threshold value, the ECU 34 is configured to cause the index value to be displayed in numerical form on a display, such as display 36, for the user to see and interpret. Once the index value is displayed, the ECU 34 is configured to repeat the above described methodology using R, X, and P samples corresponding to a subsequent point in time in the lesion formation process.

With reference to 7 and 8, in an exemplary embodiment, the method further includes a step 140 of assessing the stability of the catheter 18, and therefore, the electrodes 16, 52, 54 thereof. The stability may be assessed based on predetermined stability criteria and using techniques such as those described in greater detail above. In an exemplary embodiment wherein the stability of the catheter 18 is assessed, the method comprises performing one or more of the steps described above only when the stability of the catheter 18, and therefore, the electrodes 16, 52, 54 thereof, meets predetermined stability criteria, otherwise the stability is continuously assessed until the catheter 18 is stable and the remainder of the methodology can be performed.

With reference to FIGS. 9 and 10, alternate embodiments of the method illustrated in FIG. 5 will be described. In these particular embodiments, rather than calculating the index based on values of one or more components of the complex impedance between the electrode 16 and the tissue 12, and the value(s) of the power applied to the tissue, the index is calculated based on values for a single component of the complex impedance. Accordingly, as will be described in greater detail below, in one embodiment, the method comprises calculating the index based on two or more values of the reactance (X) between the electrode 16 and the tissue 12 corresponding to two or more points in time during a lesion formation process. It will be appreciated, however, that while the description below is directed to a method in which the calculation of the index is based solely on the reactance component of the complex impedance, those of ordinary skill in the art will appreciate that in other embodiments, components of the complex impedance other than reactance may be used to calculate the index. Therefore, the description below is provided for exemplary purposes only and is not meant to be limiting in nature. Additionally, in an exemplary embodiment the ECU 34 is configured to perform all of the steps of the methodology. However, it will be appreciated that in other exemplary embodiments, the ECU 34 may be configured to perform only some of the functionality, while other components that are part of the system 10, or separate and distinct therefrom, but that are in communication with the system 10, and the ECU 34, in particular, may be configured the other steps of the methodology.

In one exemplary embodiment, the index equals the change in the reactance (dX) over a time interval. In one embodiment illustrated, for example, in FIG. 9, the reactance values used to calculate dX, and therefore, the index, are the values at the time the lesion formation process commences (i.e., time $t_1$), and a point in time subsequent to the commencement of the lesion formation process (i.e., time $t_2, t_3, \ldots t_n$). Accordingly, in this embodiment of the method, the acquiring step 100 comprises a substep 128 of acquiring the value of the reactance ($X_1$) at time $t_1$ just after the lesion formation process commences, and storing that value in a memory or other storage medium. The acquiring step 100 further includes a substep 130 of acquiring values of the reactance (i.e., $X_2$, $X_3$, ..., $X_n$) at times subsequent to time $t_1$ (i.e., time $t_2$, $t_3$, ..., $t_n$).

In this embodiment, the calculating step 104 comprises a step 132 of calculating the change in the reactance between the start of the lesion formation process and a point in time subsequent thereto. The change in reactance may be calculated for each reactance value sampled, or may be calculated after a certain number of reactance value samples are collected or after a certain amount of time has elapsed. For ease of description purposes, however, the description below will be limited to an embodiment wherein the change in reactance is calculated for each reactance value sample. It will be appreciated in view of the above, however, that the present disclosure is not limited to such an embodiment.

Accordingly, with continued reference to FIG. 9, once the reactance value $X_1$ corresponding to the commencement of the lesion formation process (i.e., time $t_1$), and the reactance value $X_2$ corresponding to a point in time subsequent to time $t_1$ (i.e., time $t_2$) are acquired, the ECU 34 is configured to perform step 132 of calculating the change in reactance between reactance value $X_2$ and reactance value $X_1$. As illustrated in FIG. 8, in this embodiment, the step 132 comprises subtracting $X_1$ from $X_2$ to calculate the index. Once the index is calculated, a step 134 of evaluating or processing the index to determine whether there is a risk or likelihood of barotrauma occurring in the tissue is performed.

More particularly, in one exemplary embodiment, the step 134 comprises determining whether the change value is a positive or a negative value. If the value is positive, then it may be determined that there has not been a decrease in the reactance, and therefore, there is currently no likelihood of barotrauma occurring in the tissue. The methodology may then be repeated for the next reactance value sampled at a subsequent point in time (e.g., time $t_3$), and so on and so forth. If, however, the change value is negative, it may be determined that the reactance has decreased, and therefore, there is a risk or likelihood of barotrauma occurring.

Whether or not it has been determined that there is a likelihood of barotrauma occurring in the tissue, in a step 136, the ECU 34 may be configured to generate a warning or alert signal or indicator corresponding to the determination made with respect to the likelihood of barotrauma occurring in the tissue, and to control a display device, such as the display 36, to display the alert or warning represented by the signal generated by the ECU 34. Thus, the alert or indicator displayed on the display device will correspond to the determination made as to the likelihood of barotrauma occurring in the tissue (i.e., there is or is not a likelihood of barotrauma occurring in the tissue). Additionally, or in the alternative, the value of the index may be displayed for the user to see and interpret.

With reference to FIG. 10, in another exemplary embodiment, rather than calculating the change in the reactance based on the reactance value at the commencement of the lesion formation process and the reactance value corresponding to a time subsequent thereto, the method comprises calculating the change in reactance, and therefore the index, based on a current reactance value (e.g., $X_2$) (i.e., a reactance value between the electrode 16 and the tissue 12 at the time of the calculation, or a previous reactance sampled more recently than the sampling of the other reactance value (e.g., $X_1$) being taken into account) and a prior reactance value (e.g., $X_1$) sampled at a point in time after the start of the lesion formation process but before the sampling of the current reactance value (e.g., $X_2$). In such an embodiment, and as described above, the value of the reactance between the electrode 16 and the tissue 12 may be sampled at a predetermined rate, and the sampled values may be stored in a memory or storage device described elsewhere herein. As with the embodiment described above and illustrated in FIG. 9, the change in reactance may be calculated for each reactance value sampled, or may be calculated after a certain number of reactance value samples have been collected or after a certain amount of time has elapsed. For ease of description purposes, however, the description below will be limited to an embodiment wherein the change in reactance is calculated after each reactance value sample is collected. It will be appreciated in view of the above, however, that the present disclosure is not limited to such an embodiment.

Accordingly, with continued reference to FIG. 10, in this embodiment of the method, the acquiring step 100 comprises a substep 130' of acquiring a current reactance value $X_2$. This value may be received from the complex impedance sensor 64 or be obtained from a memory or storage medium. The step 100 further comprises a substep 128' of acquiring a reactance value $X_1$ corresponding to a time prior to that at which the reactance value $X_2$ was sampled. This value may be obtained from a memory or storage medium. The prior reactance value $X_1$ may be the most immediate prior reactance value to the current reactance value $X_2$, or may be another prior reactance value chosen based on certain criteria (e.g., a value acquired a certain amount of time prior to the current time, a value acquired a certain number of collected samples prior, etc.). In any event, once the acquiring substeps 128', 130' are performed, the calculating step 104, which comprises a step 132 of calculating the change in reactance, and therefore, the index, a step 134 of evaluating or processing the index, and, in an exemplary embodiment, a step 136 of generating/displaying an alert or indicator are performed. These steps may be performed in the same manner described above with respect to FIG. 9. Accordingly, the description of these steps will not be repeated here.

In another exemplary embodiment, rather than calculating the index based on the change in the reactance alone, the method comprises calculating the index by calculating the slope of a line between two reactance values corresponding to two different points in time (i.e., index=slope). As with the embodiment described above, in one exemplary embodiment illustrated in FIG. 9, the reactance values used to calculate the slope, and therefore, the index, are the values at the time the lesion formation process commences (i.e., time $t_1$), and a point in time subsequent to the commencement of the lesion formation process (i.e., time $t_2$, $t_3$, ..., $t_n$). Accordingly, in this embodiment, the acquiring step 100 comprises a substep 128 of acquiring the value of the reactance $X_1$ at time $t_1$ just after the commencement of the lesion formation process, and storing that value in a memory or some other storage medium. The step 100 further comprises a substep 130 of acquiring values of the reactance (i.e., $X_2$, $X_3$, ..., $X_n$) at times subsequent to time $t_1$ (i.e., time $t_2$, $t_3$, ..., $t_n$). As with the reactance $X_1$, each reactance value may be stored in a memory or storage medium along with its corresponding time. Accordingly, the value of the reactance is sampled at a predetermined rate following the commencement of the lesion formation process.

As briefly described above, once the acquiring substeps 128, 130 are performed, the calculating step 104 comprising a step 132 of calculating the slope of the line between a reactance value at the commencement of the lesion formation process, and a reactance value at a point in time subsequent thereto, is performed. The slope may be calculated for each reactance value sampled, or may be calculated after a certain number of reactance value samples have been collected or after a certain amount of time has elapsed. For ease of description purposes, however, the description below will be limited to an embodiment wherein the slope is calculated after each reactance value sample is collected. It will be appreciated in view of the above, however, that the present disclosure is not limited to such an embodiment.

Accordingly, with continued reference to FIG. 8, once the reactance value $X_1$ corresponding to the commencement of the lesion formation process (i.e., time $t_1$), and a reactance value $X_2$ corresponding to a point in time subsequent to time $t_1$ (i.e., time $t_2$) have been acquired, the calculating step 104 comprises a step 132 of calculating the slope (m) of the line between these two reactance values using equation (6) set forth above. Accordingly, in this embodiment, the calculating step 132 comprises calculating the change in reactance and the change in time, and then dividing the change in reactance by the change in time to solve for the slope, and therefore, the index. Once the index is calculated, the method comprises a step 134 of evaluating the index to determine whether there is a likelihood of barotrauma occurring in the tissue. More particularly, a determination is made as to whether the slope value is a positive or a negative value. If the value is positive, then the determination can be made that there has not been a decrease in the reactance, and therefore, there is currently no risk or likelihood of barotrauma occurring in the tissue. The above-described methodology may then be repeated for the next reactance value sampled at a subsequent point in time (i.e., time $t_3$), and so on and so forth. If, however, the slope value is negative, the determination can be made that the reactance has decreased, and therefore, there is a likelihood of barotrauma occurring. In either instance, and as described above, the method may further include a step 136 of generating and displaying an alert or indicator representative of the determination made with respect to the likelihood of barotrauma occurring in the tissue. Additionally, or in the alternative, the value of the index may be displayed for the user to see and interpret.

With reference to FIG. 10, in another exemplary embodiment, rather than calculating the slope based on the reactance value at the commencement of the lesion formation process and the reactance value corresponding to a time subsequent thereto, the method comprises calculating the slope, and therefore the index, based on a current reactance value (e.g., $X_2$) (i.e., a reactance value between the electrode 16 and the tissue 12 at the time of the calculation, or a previous reactance sampled more recently than the other reactance value (e.g., $X_1$) being taken into account) and a prior reactance value (e.g., $X_1$) corresponding to a point in time after the start of the lesion formation process but before the sampling of the current reactance value (e.g., $X_2$). In such an embodiment, and as described above, the value of the reactance between the electrode 16 and the tissue 12 is sampled at a predetermined rate, and each sampled value may be stored in a memory or storage device along with its corresponding time. As with the embodiment described above and illustrated in FIG. 9, the method may comprise calculating the slope for each reactance value sampled, or calculating the slope after a certain number of reactance value samples have been collected, or after a certain amount of time has elapsed. For ease of description purposes, however, the description below will be limited to an embodiment wherein the slope is calculated for each reactance value sample. It will be appreciated in view of the above, however, that the present disclosure is not limited to such an embodiment.

Accordingly, with continued reference to FIG. 10, in this embodiment, the acquiring step 100 comprises a sub step 130' of acquiring a current reactance value $X_2$. This value may be received from the complex impedance sensor 64, or may be obtained from a memory or storage medium. The acquiring step 100 further comprises a substep 128' of acquiring a reactance value $X_1$ corresponding to a point in time prior to that at which the reactance value $X_2$ was sampled. This value may be obtained from a memory or storage medium. The prior reactance value $X_1$ may be the most immediate prior reactance value to the current reactance value $X_2$, or may be another prior reactance value chosen based on certain criteria (e.g., a value acquired a certain amount of time prior to the current time, a value acquired a certain number of collected samples prior, etc.). In any event, once the acquiring substeps 128', 130' have been performed, the calculating step 104, which comprises a step 132 of calculating the slope, and therefore, the index, a step 134 of evaluating the index, and in an exemplary embodiment, a step 136 of generating and displaying an alert or indicator representative of the index are performed in the same manner described above with respect to FIG. 9. Accordingly, the description of these steps will not be repeated here.

With continued reference to FIGS. 9 and 10, whether the index comprises the change in reactance or the slope of the line between two reactance values, in an exemplary embodiment, the evaluating step 134 of the method further comprises a substep 138 of comparing the index to a threshold value, and to then determine whether, based on the comparison, there is a likelihood of barotrauma occurring in the tissue. Accordingly, rather than determining whether there is a risk or likelihood of barotrauma based solely on the index value alone, the determination is made based on a comparison of the index with a threshold value.

With reference to 9 and 10, in an exemplary embodiment, the method further includes a step 140 of assessing the stability of the catheter 18, and therefore, the electrodes 16, 52, 54 thereof. The stability may be assessed based on predetermined stability criteria and using techniques such as those described in greater detail above. In an exemplary embodiment wherein the stability of the catheter 18 is assessed, the method comprises performing one or more of the steps described above only when the stability of the catheter 18, and therefore, the electrodes 16, 52, 54 thereof, meets predetermined stability criteria, otherwise the stability is continuously assessed until the catheter 18 is stable and the remainder of the methodology can be performed It should be noted that the process described above is a lesion-by-lesion process. As such, for each new lesion that is performed during an ablation process (multiple lesions may be performed during a single ablation process), the values for the factors used in the equation for calculating the index, such as, for example, the values for $R_0$, $R_1$, $X_1$, and $P_1$ in the embodiment wherein equation (3) or (4) is used, must be reevaluated and reset in order for the calculated index to be accurate. In order for the system 10, and the ECU 34, in particular, to know when a new lesion is being performed, and therefore, when to reset and/or reevaluate the appropriate values or factors, the system 10 may further include a means or mechanism for informing the ECU 34 that a new lesion formation process is commencing. In an exemplary embodiment, the system 10 includes a user input device, such as, for example and without limitation, a trigger mechanism on the handle 44 of the catheter 42, a button associated with the visualization, mapping, and navigation system 32, or a device such as that described above with respect to user input device 82, that is electrically connected to, and configured for communication with, the ECU 34 to allow the user to indicate when a new lesion formation process is commencing. Alternatively, this may be carried out algorithmically by having the system 32, for example, determine the start of a lesion based on detection of catheter stability or some other factor/attribute. In yet another embodiment, the system 10 is configured, based on the input to ECU 34 from the ablation generator 26, to determine when one lesion formation process is concluded, and when another lesion formation process is commencing. Accordingly, it is contemplated that any number of means or mechanisms could be used to inform the ECU 34 that a lesion formation process is about commence, or has commenced, and each of these means/mechanisms remain within the spirit and scope of the present disclosure.

It should be understood that the system 10, particularly ECU 34, as described above may include conventional processing apparatus known in the art, capable of executing pre-programmed instructions stored in an associated memory, all performing in accordance with the functionality described herein. It is contemplated that the methods described herein, including without limitation the method steps of embodiments of the invention, will be programmed in a preferred embodiment, with the resulting software being stored in an associated memory and where so described, may also constitute the means for performing such methods. Implementation of the invention, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Although several embodiments of this disclosure have been described above with a certain degree of particularity, those skilled in the art could make numerous alterations to the disclosed embodiments without departing from the scope of this disclosure. All directional references (e.g., upper, lower, upward, downward, left, right, leftward, rightward, top, bottom, above, below, vertical, horizontal, clockwise and counterclockwise) are only used for identification purposes to aid the reader's understanding of the present disclosure, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for determining a likelihood of barotrauma occurring in a tissue during formation of a lesion in said tissue as a result of an ablation procedure being performed thereon, comprising:
an electronic control unit (ECU) configured to:
acquire at least one value for at least one component of a complex impedance between an electrode and said tissue; and
calculate an index responsive to said at least one value for at least one component of said complex impedance, said index indicative of said likelihood of barotrauma occurring in said tissue;
wherein said ECU is further configured to assess stability of said electrode based on predetermined stability criteria, and said calculated index is responsive to a determination by said ECU that said electrode meets said predetermined stability criteria.

2. The system of claim 1, wherein said electronic control unit is further configured to: acquire a value for power applied to said tissue during the formation of said lesion in said tissue; and said calculated index is responsive to said at least one value for at least one component of said complex impedance further using said value for power.

3. The system of claim 1, wherein said electronic control unit is configured to acquire values for first and second components of said complex impedance, said value for said first component of said complex impedance comprising said at least one value for at least one component of said complex impedance, and said calculated index is responsive to said at least one value for at least one component of said complex impedance further using said value for said second component of said complex impedance.

4. The system of claim 3, wherein said first and second complex impedance components collectively comprise two members of the group including the following members: a resistance between said electrode and said tissue, a reactance between said electrode and said tissue, a phase angle between said electrode and said tissue, and an impedance magnitude between said electrode and said tissue.

5. The system of claim 1, wherein said electrode comprises an ablation electrode on a radio-frequency ablation catheter.

6. The system of claim 1, wherein said electronic control unit is further configured to output said index to a display device.

7. The system of claim 1, wherein said electronic control unit is further configured to evaluate said index to determine said likelihood of barotrauma occurring in said tissue.

8. The system of claim 7, wherein said electronic control unit is further configured to: generate a signal representative of an indicator corresponding to said determined likelihood of barotrauma occurring in said tissue; and output said signal to a display device.

9. The system of claim 1, wherein said at least one component of said complex impedance is reactance, and said electronic control unit is configured to calculate one of a change in said reactance between a first reactance value and a second reactance value, and a slope of a line between said first reactance value and said second reactance value, wherein said one of said change in reactance and said slope comprises said index.

10. An article of manufacture, comprising:
a non-transitory computer-readable storage medium encoded with instructions:
determining a likelihood of barotrauma occurring in a tissue during formation of a lesion in said tissue as a result of an ablation procedure being performed thereon;
calculating an index responsive to at least one value of at least one component of a complex impedance between said tissue and an electrode;
assessing stability of said electrode based on predetermined stability criteria; and
said calculated index is responsive to a determination that said electrode meets said predetermined stability criteria.

11. The article of manufacture of claim 10, wherein said instructions encoded on said non-transitory computer-readable storage medium include code for evaluating said index to determine said likelihood of barotrauma occurring in said tissue.

12. The article of manufacture of claim 11, wherein said instructions encoded on said non-transitory computer-readable storage medium include code for: generating a signal representative of an indicator corresponding to said determined likelihood of barotrauma; and outputting said signal to a display device.

13. The article of manufacture of claim 10, wherein said at least one component of said complex impedance comprises reactance between said tissue and said electrode, said instructions on said non-transitory computer-readable storage medium including code for calculating said index by calculating at least one of a change in said reactance between a first reactance value and a second reactance value, and a slope of a line between said first reactance value and said second reactance value.

14. A method for determining a likelihood of barotrauma occurring in a tissue during formation of a lesion in said tissue as a result of an ablation procedure being performed thereon, comprising the steps of:
acquiring at least one value for at least one component of a complex impedance between an electrode and said tissue using an electronic control unit (ECU); and
calculating an index using said ECU, responsive to said at least one value for at least one component of said complex impedance, said index indicative of said likelihood of barotrauma occurring in said tissue;
wherein said ECU is further configured to assess stability of said electrode based on predetermined stability criteria, and said calculated index is responsive to a determination by said ECU that said electrode meets said predetermined stability criteria.

15. The method of claim 14 further comprising the step of acquiring a value for the power applied to said tissue during the formation of said lesion in said tissue, and said calculating step comprising calculating said index responsive to said at least one value for at least one component of said complex impedance and said value of said power.

16. The method of claim 14, wherein said step of acquiring at least one value for at least one component of said complex impedance comprises acquiring values for first and second components of said complex impedance, said value for said first component of said complex impedance comprising said at least one value for at least one component of said complex impedance.

17. The method of claim 14 further comprising the step of evaluating said index to determine said likelihood of barotrauma occurring in said tissue.

18. The method of claim 17 further comprising the steps of: generating a signal representative of said determined likelihood of barotrauma occurring in said tissue; and outputting said signal to a display device.

19. The method of claim 14, wherein said at least one value for at least one component of said complex impedance is reactance between said electrode and said tissue, and further wherein: said acquiring step comprising the substeps of:
acquiring a first reactance value corresponding to a first point in time; and
acquiring a second reactance value corresponding to a second point in time subsequent to said first point in time; and
said calculating said index comprises one of:
calculating a change in reactance value between said first and second reactance values by subtracting said first reactance value from said second reactance value, said change in reactance comprising said index; and
calculating a slope of a line between said first and second reactance values by subtracting said first reactance value from said second reactance value, subtracting said first point in time from said second time, and dividing said change in reactance by a change in time between said first and second points in time, said slope comprising said index.

20. An automated guidance system, comprising:
a catheter manipulator assembly;
a catheter associated with said catheter manipulator assembly, said catheter including an electrode associated therewith configured to deliver radiofrequency (RF) power to a tissue in a body; and
a controller configured to control at least one of movement of the catheter and delivery of said RF power to said tissue by said electrode in response to an index calculated from at least one value of at least one component of a complex impedance between said electrode and said tissue;
wherein said controller is configured to control at least one of the movement of the catheter and the delivery of said RF power to said tissue by said electrode in response to said index calculated from said at least one value of said at least one component of said complex impedance, and a value of said RF power applied to said tissue during formation of a lesion in said tissue.

21. The system of claim 20 wherein said catheter manipulator assembly is a robotic catheter manipulator assembly including a robotic catheter device cartridge.

22. The system of claim 20 wherein said catheter further comprises a magnetic element, and said automated catheter manipulator assembly comprises a magnetic field generator configured to generate a magnetic field to control movement of said magnetic element.

23. A system for determining a likelihood of barotrauma occurring in a tissue during formation of a lesion in said tissue as a result of an ablation procedure being performed thereon, comprising:
an electronic control unit (ECU) configured to:
acquire at least one value for at least one component of a complex impedance between an electrode and said tissue; and
calculate an index responsive to said at least one value for at least one component of said complex impedance, said index indicative of said likelihood of barotrauma occurring in said tissue;
wherein said ECU is further configured to acquire a value for power applied to said tissue during the formation of said lesion in said tissue; and said calculated index is responsive to said at least one value for at least one component of said complex impedance further using said value for power.

* * * * *